(12) United States Patent
Sasaki et al.

(10) Patent No.: US 10,092,655 B2
(45) Date of Patent: Oct. 9, 2018

(54) CATIONIC LIPID FOR NUCLEIC ACID DELIVERY

(71) Applicants: NOF CORPORATION, Tokyo (JP); NATIONAL UNIVERSITY CORPORATION HOKKAIDO UNIVERSITY, Sapporo-shi, Hokkaido (JP)

(72) Inventors: Shota Sasaki, Kawasaki (JP); Masaki Ota, Kawasaki (JP); Kazuhiro Kubo, Kawasaki (JP); Hideyoshi Harashima, Sapporo (JP); Hidetaka Akita, Sapporo (JP); Hiroto Hatakeyama, Sapporo (JP); Yuki Noguchi, Sapporo (JP); Kota Tange, Kawasaki (JP); Yuta Nakai, Kawasaki (JP); Nayuta Shimizu, Sapporo (JP)

(73) Assignees: NOF CORPORATION, Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 54 days.

(21) Appl. No.: 15/504,239

(22) PCT Filed: Aug. 7, 2015

(86) PCT No.: PCT/JP2015/072476
§ 371 (c)(1),
(2) Date: Feb. 15, 2017

(87) PCT Pub. No.: WO2016/027699
PCT Pub. Date: Feb. 25, 2016

(65) Prior Publication Data
US 2017/0274086 A1    Sep. 28, 2017

(30) Foreign Application Priority Data

Aug. 18, 2014   (JP) .................. 2014-166041

(51) Int. Cl.
*C12P 7/64*     (2006.01)
*A61K 9/107*    (2006.01)
*A61K 9/127*    (2006.01)
*A61K 47/48*    (2006.01)

(52) U.S. Cl.
CPC ........ *A61K 47/48046* (2013.01); *A61K 9/107* (2013.01); *A61K 9/127* (2013.01); *C12P 7/6445* (2013.01)

(58) Field of Classification Search
None
See application file for complete search history.

(56) References Cited

U.S. PATENT DOCUMENTS 5,068,120 A    11/1991   Yarger et al.

OTHER PUBLICATIONS

Gilleron et al., "Image-based analysis of lipid nanoparticle-mediated siRNA delivery, intracellular trafficking and endosomal escape," *Nat. Biotechnol.*, 31(7):638-646 (2013).
Japanese Patent Office, International Search Report in International Patent Application No. PCT/JP2015/072476 (dated Oct. 27, 2015).
European Patent Office, Extended European Search Report in European Patent Application No. 15833801.2 (dated Feb. 21, 2018).

*Primary Examiner* — Robert M Kelly
(74) *Attorney, Agent, or Firm* — Leydig, Voit & Mayer, Ltd.

(57) ABSTRACT

The invention provides a cationic lipid capable of achieving higher intracellular delivery efficiency than conventional cationic lipids, when used as a lipid membrane structure which is a carrier for delivering functional nucleic acid. The cationic lipid is represented by the formula (1):

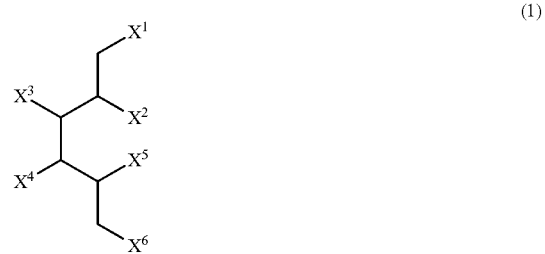

wherein each symbol is as defined herein.

9 Claims, 3 Drawing Sheets

CATIONIC LIPID FOR NUCLEIC ACID DELIVERY

CROSS-REFERENCE TO RELATED APPLICATIONS

This patent application is the U.S. national phase of International Patent Application No. PCT/JP2015/072476, filed on Aug. 7, 2015, which claims the benefit of Japanese Patent Application No. 2014-166041, filed on Aug. 18, 2014, the disclosures of which are incorporated herein by reference in their entireties for all purposes.

TECHNICAL FIELD

The present invention relates to a cationic lipid for nucleic acid delivery, a lipid membrane structure containing same, and use thereof.

BACKGROUND ART

Nucleic acid pharmaceuticals suppress expression of pathogenic proteins by delivering functional nucleic acids into the cytoplasm, are attracting attention as pharmaceuticals of the next generation, and have been studied extensively. Carriers are indispensable since functional nucleic acids have low stability in blood and are rapidly decomposed. Carriers for delivering nucleic acids include, for example, lipid membrane structures such as virus, polymer micelle, liposome and the like.

Viral carriers are most widely used for their high expression efficiency; however, they have pathogenicity and antigenicity, and functionality cannot be imparted easily. Therefore, development of a safer non-viral carrier is required, and researches of polymer micelle, lipid membrane structure and the like are ongoing. Polymer micelle is a carrier composed of polyethylene glycol (hereinafter to be referred to as "PEG"), polyamino acid and the like, and examples of clinical development are still few.

Lipid membrane structure is a carrier composed of cationic lipid, phospholipid and the like. It is advantageous in that the composition of components constituting the carrier can be changed easily and functionality can be imparted with ease by structural modification. Plural clinical developments have been conducted so far, and it is the non-viral carrier used most generally.

To effectively deliver a functional nucleic acid into the cell by using a lipid membrane structure as a carrier, it is necessary to improve intracellular kinetics such as uptake into cells, endosomal escape capability and the like, in addition to the improvement of pharmacokinetics of lipid membrane structure such as stability in blood, tumor accumulation property and the like.

A cationic lipid which is one of the constituent components of a lipid membrane structure is used for the purpose of imparting pH responsiveness to the lipid membrane structure. By using a cationic lipid, lipid membrane structures can be stably present in the physiological environment such as blood and the like. On the other hand, under the acidic environment such as in the cell, collapse of the lipid membrane structure enables release of the drug into the cytoplasm.

Cationic lipids are roughly composed of a hydrophobic moiety and a hydrophilic moiety, and the hydrophobic moiety is a hydrophobic group such as fatty acid residue, sterol residue and the like, and the hydrophilic moiety is a cationic group such as amino group, ammonium group and the like. In particular, many structures containing two hydrophobic groups in the hydrophobic moiety and one cationic group such as amino group, ammonium group and the like in the hydrophilic moiety (two-chain type cationic lipids) are known.

As a cationic lipid to be used for a lipid membrane structure, a known compound of 1,2-Dioleoyl-3-dimethylaminopropane (hereinafter to be referred to as "DODAP"), 1,2-Dilinoleoyl-3-dimethylaminopropane (hereinafter to be referred to as "DLinDAP") and the like can be mentioned.

The amino group contained in the cationic lipid is protonated and changes to cationic as the surrounding pH decreases, thereby imparting pH responsiveness to the lipid membrane structure.

A lipid membrane structure administered to a living organism is incorporated into endosome. It is known that early endosome moves to the vicinity of the Golgi apparatus, matures into late endosome containing a large number of endoplasmic reticula and binds to lysosome. When the late endosome and the lysosome are bound, the functional nucleic acid is decomposed by the degrading enzyme in the lysosome. Therefore, for an efficient delivery of functional nucleic acids into cells, it is necessary to release functional nucleic acids from the early endosome into the cytoplasm before the binding of late endosome and lysosome occurs.

However, non-patent document 1 maintains that a lipid membrane structure encapsulating functional nucleic acid releases the functional nucleic acid into the cytoplasm only in the stage of the early endosome and the amount of release is several percent.

As shown above, despite the technical progress in this field, the intracellular nucleic acid deliverability achieved by a lipid membrane structure using conventional cationic lipid is not fully satisfactory.

Document List

Non-Patent Document non-patent document 1: Nature Biotechnology, 31, 638-646 (1 Jul. 2013)

SUMMARY OF THE INVENTION

Problems to be Solved by the Invention

An object of the present invention is to provide a cationic lipid capable of achieving higher intracellular delivery efficiency than conventional cationic lipids, when used as a lipid membrane structure which is a carrier for delivering functional nucleic acid.

Means of Solving the Problems

Generally, it is known that a lipid having a conical structure with a small hydrophilic moiety and a large hydrophobic moiety tends to transfer from a lamellar phase to an inverted hexagonal phase. In contrast, phase transition of lipid membrane from lamellar phase to inverted hexagonal phase is considered to be difficult in conventional two-chain type cationic lipids, since amino groups are protonated and positively charged in vivo, and the amino groups repel each other to expand the hydrophilic moiety. Thus, in a lipid membrane structure containing a conventional two-chain type cationic lipid, phase transition of lipid membrane does not occur easily and the membrane fusion ability between the lipid membrane structure and the endosomal membrane is poor. As a result, a nucleic acid-introducing agent containing the lipid membrane structure has a low ability to deliver functional nucleic acids into the cytoplasm.

The present inventors have conducted intensive studies of the aforementioned object and developed a cationic lipid having one or two cationic groups to suppress spread of hydrophilic moiety due to electrostatic repulsion, and introduced with 1 to 4 hydrophobic groups to enlarge the hydrophobic moiety. They have found that a lipid membrane structure comprising the cationic lipid of the present invention shows high membrane fusion ability under acidic conditions such as in vivo, and a nucleic acid-introducing agent using the lipid membrane structure shows remarkably high functional nucleic acid delivery capability into the cytoplasm than a nucleic acid-introducing agent using a lipid membrane structure containing a conventional two-chain type cationic lipid, which resulted in the completion of the present invention.

Therefore, the present invention encompasses the following.

[1] a cationic lipid represented by the formula (1):

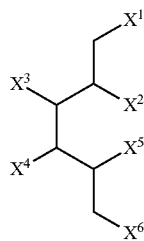

(1)

wherein any 4 of $X^1$-$X^6$ are each independently a group represented by the formula ($X^a$), a group represented by the formula ($X^b$) or a hydroxyl group (provided that said 4 are not hydroxyl groups at the same time), and the remaining 2 are each independently a group represented by the formula ($X^c$) or a hydroxyl group (provided that said 2 are not hydroxyl groups at the same time))

$$—Y^1—R^1 \quad (X^a)$$

wherein $R^1$ is an aliphatic hydrocarbon group having 8-22 carbon atoms or an acyl group having 8-22 carbon atoms; $Y^1$ is —O— or —NH—)

($X^b$)

wherein $R^2$ is a sterol residue or a liposoluble vitamin residue; $Z^1$ is an alkylene group having 2 or 3 carbon atoms; $Y^2$ is —O—CO— or —NH—CO—)

($X^c$)

wherein $R^3$ and $R^4$ are each independently an alkyl group having 1-6 carbon atoms, $R^3$ and $R^4$ are optionally bonded to form a ring; $Z^2$ is an alkylene group having 1-6 carbon atoms; $Y^3$ is —O—, —O—CO— or —NH—CO—; n is 0 or 1.

[2] The cationic lipid of [1], wherein any 4 of $X^1$-$X^6$ are each independently a group represented by the formula ($X^a$) or a group represented by the formula ($X^b$), and the remaining 2 are each independently a group represented by the formula ($X^c$).

[3] The cationic lipid of [1], wherein any 4 of $X^1$-$X^6$ are each independently a group represented by the formula ($X^a$), and the remaining 2 are each independently a group represented by the formula ($X^c$).

[4] The cationic lipid of any of [1]-[3], wherein $R^1$ is an aliphatic hydrocarbon group having 10-20 carbon atoms or an acyl group having 10-20 carbon atoms.

[5] The cationic lipid of any of [1]-[3], wherein $R^1$ is an aliphatic hydrocarbon group having an unsaturated bond and 10-20 carbon atoms or an acyl group having 10-20 carbon atoms.

[6] The cationic lipid of any of [1]-[5], wherein $Y^1$ is —O—.

[7] The cationic lipid of [1], wherein any 4 of $X^1$-$X^6$ are each independently a group represented by the formula ($X^b$), and the remaining 2 are each independently a group represented by the formula ($X^c$).

[8] A lipid membrane structure comprising the cationic lipid of any of [1]-[7].

[9] A nucleic acid-introducing agent comprising the lipid membrane structure of [8] and a nucleic acid.

Effect of the Invention

The present invention relates to a cationic lipid composed of a hydrophobic moiety containing 1 to 4 hydrophobic groups and a hydrophilic moiety containing one or two cationic groups, a lipid membrane structure containing the cationic lipid, and a nucleic acid-introducing agent containing the lipid membrane structure and a nucleic acid. The cationic lipid of the present invention can form a stable lipid membrane structure, and can adjust acid dissociation constant (hereinafter to be referred to as "pKa") of the lipid membrane structure to near neutral. Furthermore, when a functional nucleic acid is introduced by a nucleic acid-introducing agent using the cationic lipid of the present invention, the agent shows high membrane fusion ability with the endosomal membrane only under a slightly acidic environment such as in the endosome, and the functional nucleic acid can be efficiently released in the cytoplasm. That is, by introducing a functional nucleic acid by a nucleic acid-introducing agent using the cationic lipid of the present invention, efficient gene knockdown can be achieve via the functional nucleic acid delivered into the cytoplasm.

DESCRIPTION OF EMBODIMENTS

Figure 1:
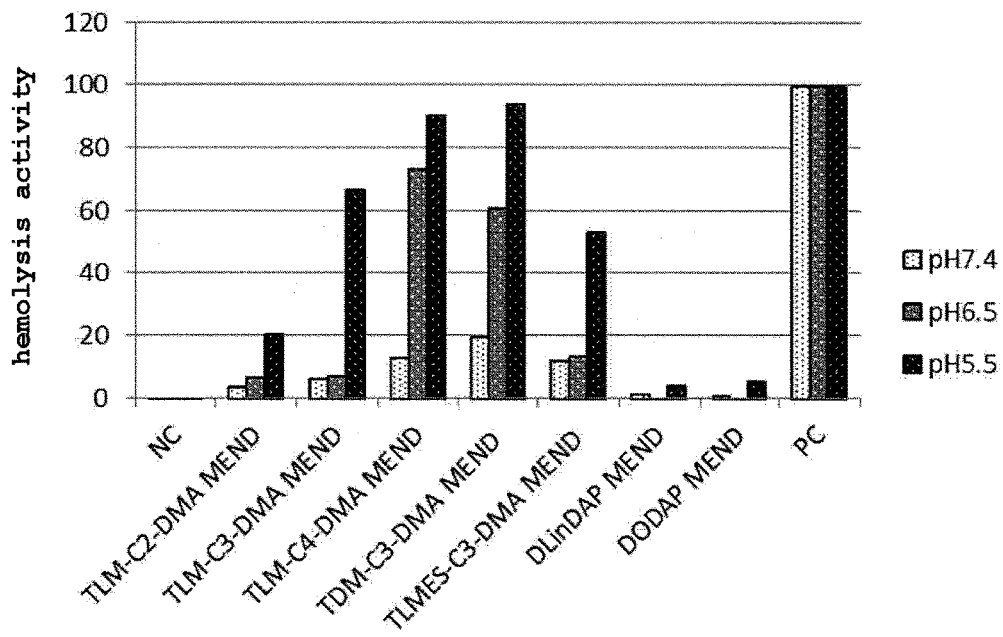
FIG. 1 is a graph showing the hemolysis activity of TLM-C2-DMA MEND, TLM-C3-DMA MEND, TLM-C4-DMA MEND, TDM-C3-DMA MEND, TLMES-C3-DMA MEND, DLinDAP MEND, DODAP MEND.

The embodiments of the present invention are explained in the following.

1. The Cationic Lipid of the Present Invention

The present invention provides a cationic lipid represented by the formula (1).

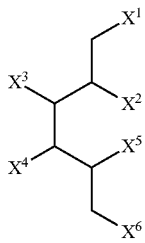

(1)

wherein any 4 of $X^1$-$X^6$ are each independently a group represented by the formula ($X^a$), a group represented by the formula ($X^b$) or a hydroxyl group (provided that said 4 are not hydroxyl groups at the same time), and the remaining 2 are each independently a group represented by the formula ($X^c$) or a hydroxyl group (provided that said 2 are not hydroxyl groups at the same time))

—$Y^1$—$R^1$ ($X^a$)

wherein $R^1$ is an aliphatic hydrocarbon group having 8-22 carbon atoms or an acyl group having 8-22 carbon atoms; $Y^1$ is —O— or —NH—)

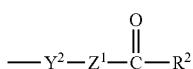

($X^b$)

wherein $R^2$ is a sterol residue or a liposoluble vitamin residue; $Z^1$ is an alkylene group having 2 or 3 carbon atoms; $Y^2$ is —O—CO— or —NH—CO—)

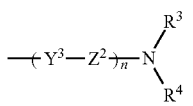

($X^c$)

wherein $R^3$ and $R^4$ are each independently an alkyl group having 1-6 carbon atoms, $R^3$ and $R^4$ are optionally bonded to form a ring; $Z^2$ is an alkylene group having 1-6 carbon atoms; $Y^3$ is —O—, —O—CO— or —NH—CO—; n is 0 or 1.

In the formula (1), any 4 of $X^1$-$X^6$ only need to be each independently a group represented by the formula ($X^a$), a group represented by the formula ($X^b$) or a hydroxyl group (provided that said 4 are not hydroxyl groups at the same time), and the remaining 2 only need to be each independently a group represented by the formula ($X^c$) or a hydroxyl group (provided that said 2 are not hydroxyl groups at the same time)), preferably, any 4 of $X^1$-$X^6$ are each independently a group represented by the formula ($X^a$), or a group represented by the formula ($X^b$), and the remaining 2 are each independently a group represented by the formula ($X^c$) or a hydroxyl group (provided that said 2 are not hydroxyl groups at the same time)), more preferably, any 4 of $X^1$-$X^6$ are each independently a group represented by the formula ($X^a$) or a group represented by the formula ($X^b$), and the remaining 2 are each independently a group represented by the formula ($X^c$).

In one embodiment of the formula (1), when any 4 of $X^1$-$X^6$ are each independently a group represented by the formula ($X^a$) or a group represented by the formula ($X^b$), and the remaining 2 are each independently a group represented by the formula ($X^c$), the combination of the group represented by the formula ($X^a$), the group represented by the formula ($X^b$) and the group represented by the formula ($X^c$) for $X^1$-$X^6$ may be any. Specific examples of the combination include the combination of the following (1)-(8).

(1) $X^1$, $X^2$, $X^5$ and $X^6$ are each independently a group represented by the formula ($X^a$), and $X^3$ and $X^4$ are each independently a group represented by the formula ($X^c$).

(2) $X^1$, $X^3$, $X^4$ and $X^6$ are each independently a group represented by the formula ($X^a$), and $X^2$ and $X^5$ are each independently a group represented by the formula ($X^c$).

(3) $X^2$, $X^3$, $X^4$ and $X^5$ are each independently a group represented by the formula ($X^a$), and $X^5$ and $X^6$ are each independently a group represented by the formula ($X^c$).

(4) $X^1$, $X^2$, $X^3$ and $X^4$ are each independently a group represented by the formula ($X^a$), and $X^5$ and $X^6$ are each independently a group represented by the formula ($X^c$).

(5) $X^1$, $X^2$, $X^5$ and $X^6$ are each independently a group represented by the formula ($X^b$), and $X^3$ and $X^4$ are each independently a group represented by the formula ($X^c$).

(6) $X^1$, $X^3$, $X^4$ and $X^6$ are each independently a group represented by the formula ($X^b$), and $X^2$ and $X^5$ are each independently a group represented by the formula ($X^c$).

(7) $X^2$, $X^3$, $X^4$ and $X^5$ are each independently a group represented by the formula ($X^b$), and $X^5$ and $X^6$ are each independently a group represented by the formula ($X^c$).

(8) $X^1$, $X^2$, $X^3$ and $X^4$ are each independently a group represented by the formula ($X^b$), and $X^5$ and $X^6$ are each independently a group represented by the formula ($X^c$).

Of these, from the aspects of easy procurement of the starting materials and easy production, the combination of (1) is preferable, particularly, the combination of (1) wherein a group represented by the formula ($X^a$) is the same for $X^1$, $X^2$, $X^5$ and $X^6$ and a group represented by the formula ($X^c$) is the same for $X^3$ and $X^4$ is preferable.

Also, from the aspects of easy procurement of the starting materials and easy production, the combination of (3) is preferable, particularly, the combination of (3) wherein a group represented by the formula ($X^a$) is the same for $X^2$, $X^3$, $X^4$ and $X^5$ and a group represented by the formula ($X^c$) is the same for $X^1$ and $X^6$ is preferable.

In one embodiment of the formula (1), when any 4 of $X^1$-$X^6$ are each independently a group represented by the formula ($X^a$) or a group represented by the formula ($X^b$), for example, one of the remaining 2 may be a group represented by the formula ($X^c$) and the other may be a hydroxyl group, or both of the remaining 2 may each be a group represented by the formula ($X^c$).

In the formula (1), the number of $X^1$-$X^6$ showing a hydroxyl group is preferably not more than 3, more preferably not more than 1, particularly preferably 0.

The definition of each group in the formula ($X^a$), formula ($X^b$) and formula ($X^c$) is described in detail below.

[Formula ($X^a$)]

The formula ($X^a$) shows a structure of —$Y^1$—$R^1$.

$R^1$ is an aliphatic hydrocarbon group having 8-22 carbon atoms or an acyl group having 8-22 carbon atoms. The number of carbons contained in the aliphatic hydrocarbon group and acyl group is preferably 10-20. The aliphatic hydrocarbon group and the acyl group may be linear or branched or have a ring, but are preferably linear. The aliphatic hydrocarbon group and the acyl group may be saturated or contain an unsaturated bond, but preferably contain an unsaturated bond. When the aliphatic hydrocarbon group and the acyl group contain an unsaturated bond, the number of unsaturated bonds contained therein is generally 1 to 6, preferably 1 to 3, more preferably 1 or 2. The unsaturated bond contained therein is preferably a carbon-carbon double bond.

Examples of the aliphatic hydrocarbon group having 8-22 carbon atoms include octyl group, nonyl group, decyl group, undecyl group, dodecyl group, tridecyl group, tetradecyl group, pentadecyl group, hexadecyl group, heptadecyl group, octadecyl group, nonadecyl group, icosyl group, henicosyl group, docosyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, octadienyl group, nonadienyl group, decadienyl group, undecadienyl group, dodecadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group, tetramethylhexadecenyl group (phytyl group) and the like. Preferred are aliphatic hydrocarbon groups having 10-20 carbon atoms, which are saturated or have an unsaturated bond, such as decyl group, dodecyl group, tetradecyl group, hexadecyl group, octadecyl group, icosyl group, decenyl group, dodecenyl group, tetradecenyl group, hexadecenyl group, octadecenyl group, icosenyl group, decadienyl group, dodecadienyl group, tetradecadienyl group, hexadecadienyl group, octadecadienyl group, icosadienyl group and the like, and more preferred are aliphatic hydrocarbon groups having an unsaturated bond and 10-20 carbon atoms, such as decenyl group, dodecenyl group, tetradecadienyl group, hexadecadienyl group, octadecadienyl group and the like.

Examples of the acyl group having 8-22 carbon atoms include octanoyl group, nonanoyl group, decanoyl group, undecanoyl group, dodecanoyl group, tridecanoyl group, tetradecanoyl group, pentadecanoyl group, hexadecanoyl group, heptadecanoyl group, octadecanoyl group, nonadecanoyl group, icosanoyl group, henicosanoyl group, docosanoyl group, octaenoyl group, nonaenoyl group, decaenoyl group, undecaenoyl group, dodecaenoyl group, tridecaenoyl group, tetradecaenoyl group, pentadecaenoyl group, hexadecaenoyl group, heptadecaenoyl group, octadecaenoyl group, nonadecaenoyl group, icosaenoyl group, henicosaenoyl group, docosaenoyl group, octadienoyl group, nonadienoyl group, decadienoyl group, undecadienoyl group, dodecadienoyl group, tridecadienoyl group, tetradecadienoyl group, pentadecadienoyl group, hexadecadienoyl group, heptadecadienoyl group, octadecadienoyl group, nonadecadienoyl group, icosadienoyl group, henicosadienoyl group, docosadienoyl group, octadecatrienoyl group, icosatrienoyl group, icosatetraenoyl group, icosapentaenoyl group, docosahexaenoyl group, isostearoyl group, tetramethylhexadecanoyl group (phytanoyl group), retinoyl group and the like. Preferred are acyl groups having 10-20 carbon atoms, which are saturated or have an unsaturated bond, such as decanoyl group, dodecanoyl group, tetradecanoyl group, hexadecanoyl group, octadecanoyl group, icosanoyl group, decaenoyl group, dodecaenoyl group, tetradecaenoyl group, hexadecaenoyl group, octadecaenoyl group, icosaenoyl group, decadienoyl group, dodecadienoyl group, tetradecadienoyl group, hexadecadienoyl group, octadecadienoyl group, icosadienoyl group and the like, and more preferred are acyl groups having an unsaturated bond and 10-20 carbon atoms, such as decaenoyl group, dodecaenoyl group, tetradecadienoyl group, hexadecadienoyl group, octadecadienoyl group and the like.

When the formula (1) contains two or more groups represented by the formula ($X^a$), respective $R^1$ may be the same or different, preferably the same.

$Y^1$ is —O— or —NH—, preferably —O—. When the formula (1) contains two or more groups represented by the formula ($X^a$), respective $Y^1$ may be the same or different, preferably the same.

A preferable group represented by the formula ($X^a$) is a group represented by the formula ($X^a$) wherein $R^1$ is an aliphatic hydrocarbon group or an acyl group having an unsaturated bond and 10-20 carbon atoms, and $Y^1$ is —O—.

When the formula (1) contains two or more groups represented by the formula ($X^a$), the groups represented by the formula ($X^a$) may be the same or different, preferably the same.

[Formula ($X^b$)]

The formula ($X^b$) shows a structure of —$Y^2$—$Z^1$—CO—$R^2$.

$R^2$ is a sterol residue or a liposoluble vitamin residue, preferably a liposoluble vitamin residue.

Examples of the sterol residue include cholesteryl group (cholesterol residue), cholestaryl group (cholestanol residue), stigmasteryl group (stigmasterol residue), β-sitosteryl group (β-sitosterol residue), lanosteryl group (lanosterol residue), ergosteryl group (ergosterol residue) and the like. The sterol residue is preferably a cholesteryl group or a cholestaryl group.

Examples of the liposoluble vitamin residue include retinol residue, retinal residue, ergosterol residue, 7-hydroxycholesterol residue, 7-dehydrocholesterol residue, calciferol residue, colecalciferol residue, dihydroergocalciferol residue, dihydrotachysterol residue, tocopherol residue, tocotrienol residue and the like. The liposoluble vitamin residue is preferably a retinol residue or a tocopherol residue.

When the formula (1) contains two or more groups represented by the formula ($X^b$), respective $R^2$ may be the same or different, preferably the same.

$Z^1$ is an alkylene group having 2 or 3 carbon atoms, and the alkylene group may be linear or optionally has a branch, but is preferably linear. Examples of the alkylene group having 2 or 3 carbon atoms include ethylene group, trimethylene group and the like, preferably trimethylene group.

When the formula (1) contains two or more groups represented by the formula ($X^b$), respective $Z^1$ may be the same or different, preferably the same.

$Y^2$ is —O—CO— or —NH—CO—, preferably —O—CO—. While the direction of the bond for $Y^2$ is not limited, for example, when $Y^2$ is —O—CO—, the formula ($X^b$) preferably shows the structure of —O—CO—$Z^1$—CO—$R^2$.

For example, when $Y^2$ is —NH—CO—, the formula ($X^b$) preferably shows the structure of —NH—CO—$Z^1$—CO—$R^2$.

When the formula (1) contains two or more groups represented by the formula ($X^b$), respective $Y^2$ may be the same or different, preferably the same.

A preferable group represented by the formula ($X^b$) is a group represented by the formula ($X^b$) wherein $R^2$ is a sterol residue (preferably cholesteryl group or cholestaryl group) or a liposoluble vitamin residue (preferably retinol residue or tocopherol residue), $Z^1$ is an alkylene group having 2 or 3 carbon atoms (preferably ethylene group or trimethylene group, more preferably trimethylene group), and $Y^2$ is —O—CO—.

When the formula (1) contains two or more groups represented by the formula ($X^b$), the groups represented by the formula ($X^b$) may be the same or different, preferably the same.

[Formula ($X^c$)]

The formula ($X^c$) shows the structure of —($Y^3$—$Z^2$)$_n$—$NR^3R^4$.

$R^3$ and $R^4$ are each independently an alkyl group having 1-6 carbon atoms. $R^3$ and $R^4$ may be any of linear, branched chain and cyclic, and $R^3$ and $R^4$ may be bonded to each other to form a ring. The carbon number of the alkyl group is preferably 1-3. Examples of the linear or branched chain alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. Specific examples of —$NR^3R^4$ when $R^3$ and $R^4$ are bonded to each other to form a ring include aziridyl group, azetidyl group, azolidyl group, piperidyl group and the like. $R^3$ and $R^4$ are each preferably a methyl group, an ethyl group, a propyl group or an isopropyl group, more preferably a methyl group.

$R^3$ and $R^4$ may be the same or different, and $R^3$ and $R^4$ are preferably the same.

When the formula (1) contains two groups represented by the formula ($X^c$), respective $R^3$ may be the same or different, preferably the same.

When the formula (1) contains two groups represented by the formula ($X^c$), respective $R^4$ may be the same or different, preferably the same.

$Z^2$ is an alkylene group having 1-6 carbon atoms. $Z^2$ may be linear or optionally has a branch, but is preferably linear. Examples of the alkylene group having 1-6 carbon atoms include methylene group, ethylene group, trimethylene group, isopropylidene group, tetramethylene group, isobutylene group, pentamethylene group, neopentylene group, hexamethylene group and the like. $Z^2$ is preferably a methylene group, an ethylene group, a trimethylene group, an isopropylidene group, a tetramethylene group or a hexamethylene group, more preferably an ethylene group or a trimethylene group.

When the formula (1) contains two groups represented by the formula ($X^c$), respective $Z^2$ may be the same or different, preferably the same.

$Y^3$ is —O—, —O—CO— or —NH—CO—, preferably —O—CO—. While the direction of the bond for $Y^3$ is not limited, for example, when $Y^3$ is —O—CO—, the formula ($X^c$) preferably shows the structure of —(O—CO—$Z^2$)$_n$—$NR^3R^4$. When $Y^3$ is —O—, the formula ($X^c$) preferably shows the structure of —(O—$Z^2$)$_n$—$NR^3R^4$ and when $Y^3$ is —NH—CO—, the formula ($X^c$) preferably shows the structure of —(NH—CO—$Z^2$)$_n$—$NR^3R^4$.

When the formula (1) contains two groups represented by the formula ($X^c$), respective $Y^3$ may be the same or different, preferably the same.

n is 0 or 1, preferably 1. When n is 1, the formula ($X^c$) shows the structure of —$Y^3$—$Z^2$—$NR^3R^4$, and when n is 0, the formula ($X^c$) shows the structure of —$NR^3R^4$.

When the formula (1) contains two groups represented by the formula ($X^c$), respective n may be the same or different, preferably the same.

A preferable group represented by the formula ($X^c$) is a group represented by the formula ($X^c$) wherein $R^3$ and $R^4$ are independently an alkyl group having 1-3 carbon atoms (preferably methyl group, ethyl group, propyl group or isopropyl group, more preferably methyl group), $Z^2$ is an alkylene group having 1-6 carbon atoms (preferably methylene group, ethylene group, trimethylene group, isopropylidene group, tetramethylene group, hexamethylene group, more preferably ethylene group, trimethylene group), $Y^3$ is —O—CO—, and n is 1.

When the formula (1) contains two groups represented by the formula ($X^c$), the groups represented by the formula ($X^c$) may be the same or different, preferably the same.

Specific examples of the cationic lipid of the present invention include TLM-C2-DMA (1,2,5,6-tetralinoleyl-3,4-di(dimethylaminoacetyl)-D-mannitol), TLM-C3-DMA (1,2,5,6-tetralinoleyl-3,4-di(3-dimethylaminopropanoyl)-D-mannitol), TLM-C4-DMA (1,2,5,6-tetralinoleyl-3,4-di(4-dimethylaminobutanoyl)-D-mannitol), TDM-C3-DMA (1,2,5,6-tetrakis(decenyl)-3,4-di(3-dimethylaminopropanoyl)-D-mannitol), TLMES-C3-DMA (tetralinoleoyl-di(3-dimethylaminopropanoyl)-D-mannitol) and the like described in Table 1.

TABLE 1

| name of cationic lipid | structure |
| --- | --- |
| TLM-C2-DMA | 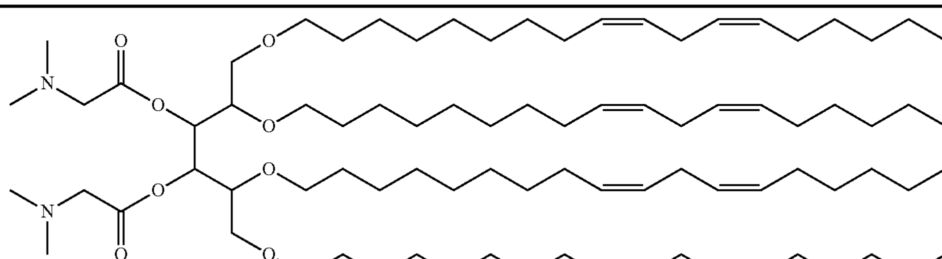 |

TABLE 1-continued

| name of cationic lipid | structure |
|---|---|
| TLM-C3-DMA | 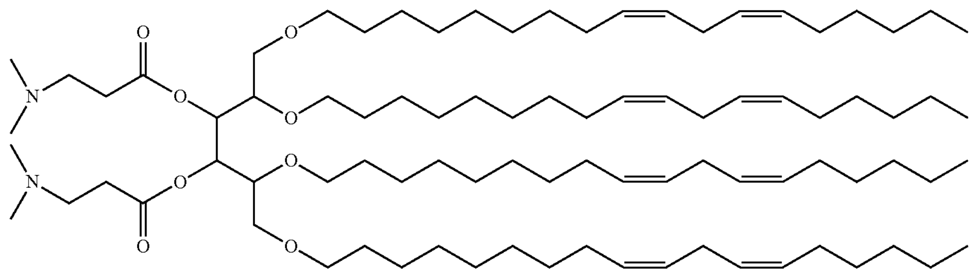 [SMILES: CCCCC/C=C\C/C=C\CCCCCCCCOCC(OCCCCCCCC/C=C\C/C=C\CCCCC)C(OC(=O)CCN(C)C)C(OC(=O)CCN(C)C)C(COCCCCCCCC/C=C\C/C=C\CCCCC)OCCCCCCCC/C=C\C/C=C\CCCCC] |
| TLM-C4-DMA | 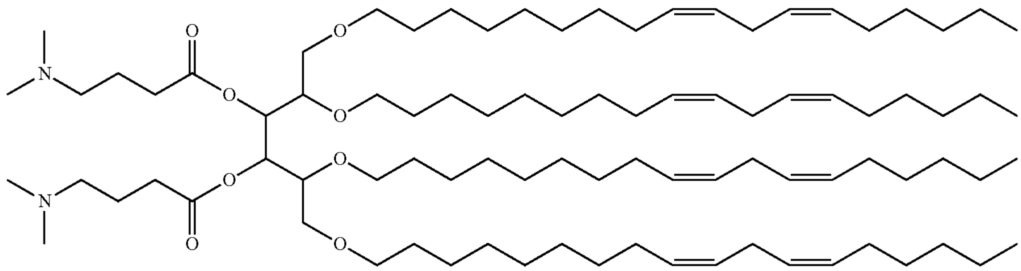 [SMILES: CCCCC/C=C\C/C=C\CCCCCCCCOCC(OCCCCCCCC/C=C\C/C=C\CCCCC)C(OC(=O)CCCN(C)C)C(OC(=O)CCCN(C)C)C(COCCCCCCCC/C=C\C/C=C\CCCCC)OCCCCCCCC/C=C\C/C=C\CCCCC] |
| TDM-C3-DMA | 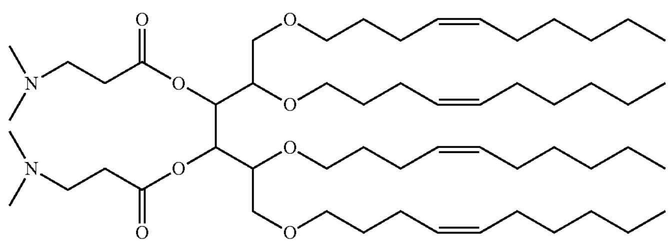 [SMILES: CCCCC/C=C\CCCOCC(OCCC/C=C\CCCCC)C(OC(=O)CCN(C)C)C(OC(=O)CCN(C)C)C(COCCC/C=C\CCCCC)OCCC/C=C\CCCCC] |
| TLMES-C3-DMA | 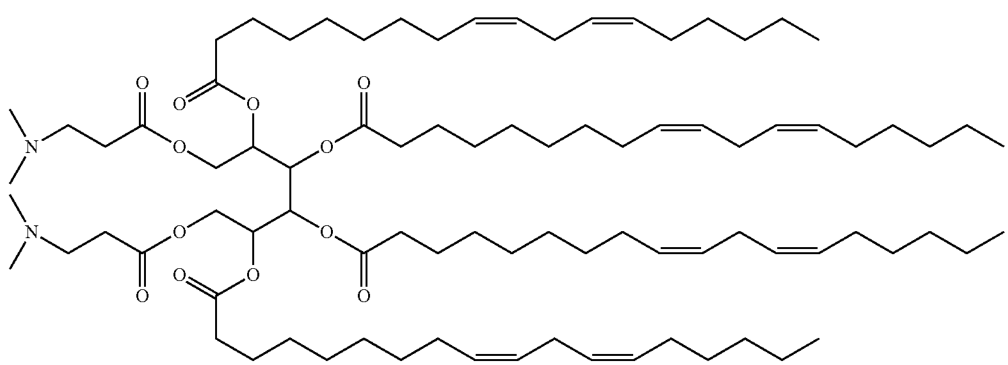 [SMILES: CCCCC/C=C\C/C=C\CCCCCCCC(=O)OC(COC(=O)CCN(C)C)C(OC(=O)CCCCCCC/C=C\C/C=C\CCCCC)C(OC(=O)CCCCCCC/C=C\C/C=C\CCCCC)C(COC(=O)CCN(C)C)OC(=O)CCCCCCC/C=C\C/C=C\CCCCC] |

The production method of the cationic lipid of the present invention is explained below.

The production method of the cationic lipid of the present invention comprises, for example, introducing a group represented by the formula ($X^a$) and/or a group represented by the formula ($X^b$), and a group represented by the formula ($X^c$) into a compound represented by the formula (1') and having 6 hydroxyl groups, and examples thereof include (i) a method for introducing $X^a$ and/or $X^b$, and then $X^c$, (ii) a method for introducing $X^c$, and then $X^a$ and/or $X^b$, (iii) a method for simultaneously introducing $X^a$ and/or $X^b$ and $X^c$, a method analogous thereto and the like.

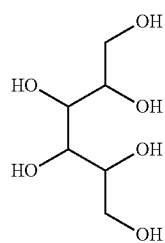

(1')

While the production method of the cationic lipid of the present invention is not particularly limited, preferred is the method of the above-mentioned (i). While specific examples of the method (i) are shown below, the production method of the cationic lipid of the present invention is not particularly limited by those methods.

Examples of the starting compound include a compound represented by the formula (1') and having 6 hydroxyl groups, wherein two hydroxyl groups are protected by a protecting group, and a compound represented by the formula (1'), wherein 4 hydroxyl groups are protected by a protecting group and the like.

As these starting compounds, commercially available compounds can be easily obtained, or they can also be produced according to a method known per se or a method analogous thereto.

Examples of the protecting group to be introduced into the formula (1') include isopropylidene group, benzylidene group, benzoyl group, benzyl group, trityl group, 4-methoxytrityl group, 4,4'-dimethoxytrityl group, trialkylsilyl group (e.g., trimethylsilyl group, triethylsilyl group, tert-butyldimethylsilyl group, tert-butyldiphenylsilyl group etc.) and the like. While an introduction method of the protecting group is not particularly limited, it can be performed by a method known per se or a method analogous thereto.

For example, when a compound represented by the formula (5) which is the formula (1) wherein $X^1$, $X^2$, $X^5$ and $X^6$ are each a group represented by the formula ($X^a$) ($R^1$: aliphatic hydrocarbon group, $Y^1$: —O—, and other symbols are as defined for the formula ($X^c$)), and $X^3$ and $X^4$ are each a group represented by the formula ($X^c$) ($Y^3$: —CO—O—, n: 1) is produced as the cationic lipid of the present invention, the compound represented by the formula (5) can be produced using a compound represented by the formula (1a) as a starting compound and performing the following step 1 (etherification), step 2 (deprotection), step 3 (esterification), or step 1 (etherification), step 2 (deprotection), step 4 (esterification) and step 5 (amination).

trialkylsilyl group and the like), B is a leaving group (e.g., iodine atom, bromine atom, chlorine atom, methanesulfonyloxy group, p-toluenesulfonyloxy group, trifluoromethanesulfonyloxy group etc.), D is a hydroxyl group or a halogen atom (e.g., iodine atom, bromine atom, chlorine atom and the like), and E is a group represented by the formula (E) or a vinyl group.

B—$Z^2$— (B)

wherein $Z^2$ is an alkylene group having 1-6 carbon atoms, and B is a leaving group (e.g., iodine atom, bromine atom, chlorine atom, methanesulfonyloxy group, p-toluenesulfonyloxy group, trifluoromethanesulfonyloxy group and the like).

Step 1 (Etherification)

A compound represented by the formula (1a) and a compound represented by $R^1$—B wherein $R^1$ and B are as defined above are reacted to give a compound represented by the formula (2).

In the reaction, a base catalyst such as potassium hydroxide, sodium hydride, potassium t-butoxide and the like may be used, and the reaction may be performed without a catalyst. Preferably, potassium hydroxide is used as a catalyst. The amount of the catalyst to be used is generally 6-20 molar equivalents, preferably 8-12 molar equivalents, relative to a compound represented by the formula (1a).

While a solvent may be used for the reaction or the reaction may be performed without solvent, since a compound represented by the formula (1a) is a highly-polar solid, and needs to be dispersed in the reaction system, a solvent is preferably used. As the solvent, one that does not inhibit the reaction and can disperse a compound represented by the formula (1a) can be used and, for example, hexane, toluene, dimethylformamide, dimethyl sulfoxide (hereinafter to be referred to as "DMSO") and the like can be mentioned. Of these, toluene is preferable.

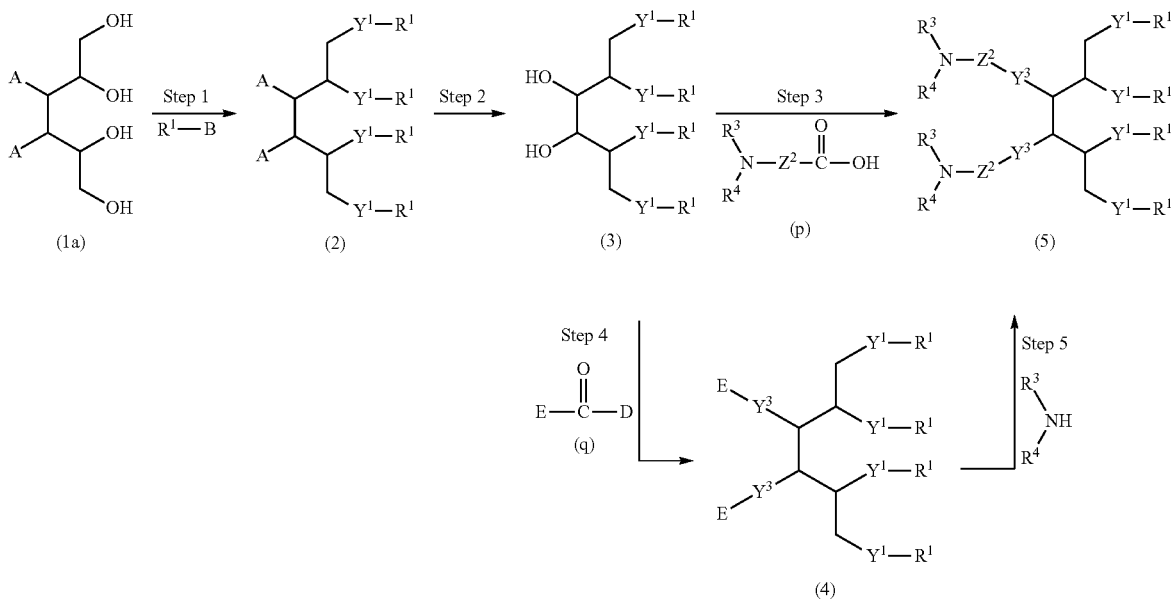

wherein, A is a protecting group (e.g., isopropylidene group, benzylidene group, benzoyl group, benzyl group, trityl group, 4-methoxytrityl group, 4,4'-dimethoxytrityl group, The reaction temperature is generally 20-150° C., preferably 40-100° C. The reaction time is generally 1-50 hr, preferably 10-30 hr.

The obtained compound represented by the formula (2) can be appropriately purified by means such as extraction, recrystallization, adsorption treatment, reprecipitation, column chromatography and the like.

Step 2 (Deprotection)

A protecting group of the compound represented by the formula (2) is removed to give a compound represented by the formula (3) containing two free hydroxyl groups.

An acid catalyst is used for the reaction. As the acid catalyst, hydrochloric acid, acetic acid, sulfuric acid, phosphoric acid, p-toluenesulfonic acid monohydrate and the like can be mentioned, and hydrochloric acid is preferable.

The amount of the catalyst to be used is generally 1-50 molar equivalents, preferably 5-20 molar equivalents, relative to a compound represented by the formula (2).

A solvent is used for the reaction. As the solvent, methanol, ethanol, isopropanol, water and the like can be mentioned, and methanol and ethanol are preferable.

The reaction temperature is generally 20-70° C., preferably 40-60° C. The reaction time is generally 1-12 hr, preferably 4-8 hr.

The obtained compound represented by the formula (3) can be appropriately purified by means such as extraction, recrystallization, adsorption treatment, reprecipitation, column chromatography and the like.

Step 3 (Esterification)

A compound represented by the formula (3) and a compound represented by the formula (p) wherein $R^3$, $R^4$ and $Z^2$ are as defined above are reacted to give a compound represented by the formula (5) of the present invention.

For the reaction, condensing agents such as dicyclohexylcarbodiimide (hereinafter to be referred to as "DCC"), diisopropylcarbodiimide (hereinafter to be referred to as "DIC"), 1-ethyl-3-(dimethylaminopropyl) carbodiimide hydrochloride (hereinafter to be referred to as "EDC") and the like are used.

A base catalyst is added for the reaction. As the base catalyst, 4-dimethylaminopyridine (hereinafter to be referred to as "DMAP"), pyridine, triethylamine and the like can be mentioned, and DMAP is preferable.

The amount of a compound represented by the formula (p) to be charged is generally 2-10 molar equivalents, preferably 4-8 molar equivalents, relative to a compound represented by the formula (3).

While a solvent may be used for the reaction or the reaction may be performed without solvent, since a compound represented by the formula (p) is a highly-polar solid, and needs to be dissolved or dispersed in the reaction system, a solvent is preferably used. As the solvent that can dissolve or disperse a compound represented by the formula (p), for example, chloroform, dichloromethane, toluene, ethyl acetate and the like can be mentioned. Of these, chloroform is preferable.

The reaction temperature is generally 10-60° C., preferably 20-40° C. The reaction time is generally 1-20 hr, preferably 2-10 hr.

The obtained compound represented by the formula (5) can be appropriately purified by means such as extraction, recrystallization, adsorption treatment, reprecipitation, column chromatography and the like.

Step 4 (Esterification)

A compound represented by the formula (3) and a compound represented by the formula (q) (wherein D and E are as defined above) are reacted to give a compound represented by the formula (4).

When D in a compound represented by the formula (q) is a hydroxyl group, a condensing agent such as DCC, DIC, EDC and the like is used for the reaction. A compound represented by the formula (3) and a compound represented by the formula (q) may be directly reacted, or an acid anhydride of a compound represented by the formula (q) may be formed and reacted with a compound represented by the formula (3).

When D in a compound represented by the formula (q) is a halogen atom, a base is added to neutralize halogenated hydrogen to be by-produced. As the base, triethylamine, pyridine and the like can be mentioned.

A solvent is used for the reaction. As the solvent, chloroform, dichloromethane, toluene, ethyl acetate and the like can be mentioned, and toluene is preferable.

The amount of a compound represented by the formula (q) to be charged is generally 2-10 molar equivalents, preferably 2-5 molar equivalents, relative to a compound represented by the formula (3).

The reaction temperature is generally 0-60° C., preferably 10-40° C., the reaction time is generally 1-10 hr, preferably 1-5 hr.

The obtained compound represented by the formula (4) can be appropriately purified by means such as extraction, recrystallization, adsorption treatment, reprecipitation, column chromatography and the like.

Step 5 (Amination)

A secondary amine containing $R^3$ and $R^4$ and a compound represented by the formula (4) are reacted to give a compound represented by the formula (5) of the present invention.

For the reaction, a base catalyst such as potassium carbonate, sodium carbonate, potassium t-butoxide and the like may be used, or the reaction may be performed without catalyst.

A solvent may be used for the reaction or the reaction may be performed without solvent. As the solvent, for example, ethyl acetate, dichloromethane, chloroform, benzene, toluene, tetrahydrofuran (hereinafter to be referred to as "THF") and the like can be used. Of these, toluene is preferable.

The amount of secondary amine containing $R^3$ and $R^4$ to be charged is generally 1-20 molar equivalents, preferably 5-10 molar equivalents relative to a compound represented by the formula (4).

The reaction temperature is generally 10-100° C., preferably 60-80° C. The reaction time is generally 1-10 hr, preferably 2-6 hr.

The obtained compound represented by the formula (5) can be appropriately purified by means such as extraction, recrystallization, adsorption treatment, reprecipitation, column chromatography and the like.

Those of ordinary skill in the art can produce a desired cationic lipid d of the present invention by appropriately selecting the starting material and performing the reactions according to the method of the Examples in the present specification.

For example, when a compound represented by the formula (9) which is the formula (1) wherein $X^2$, $X^3$, $X^4$ and $X^5$ are each a group represented by the formula ($X^a$) ($R^1$: acyl group, $Y^1$: —O—), and $X^1$ and $X^6$ are each a group represented by the formula ($X^c$) (n: 1, $Y^3$: —CO—O—, and other symbols are as defined for the formula ($X^c$)) is produced, the compound represented by the formula (9) can be produced using a compound represented by the formula (1b) as a starting compound and performing the following step 6 (esterification), step 7 (deprotection), step 8 (esterification), or step 6 (esterification), step 7 (deprotection), step 9 (esterification), and step 10 (amination).

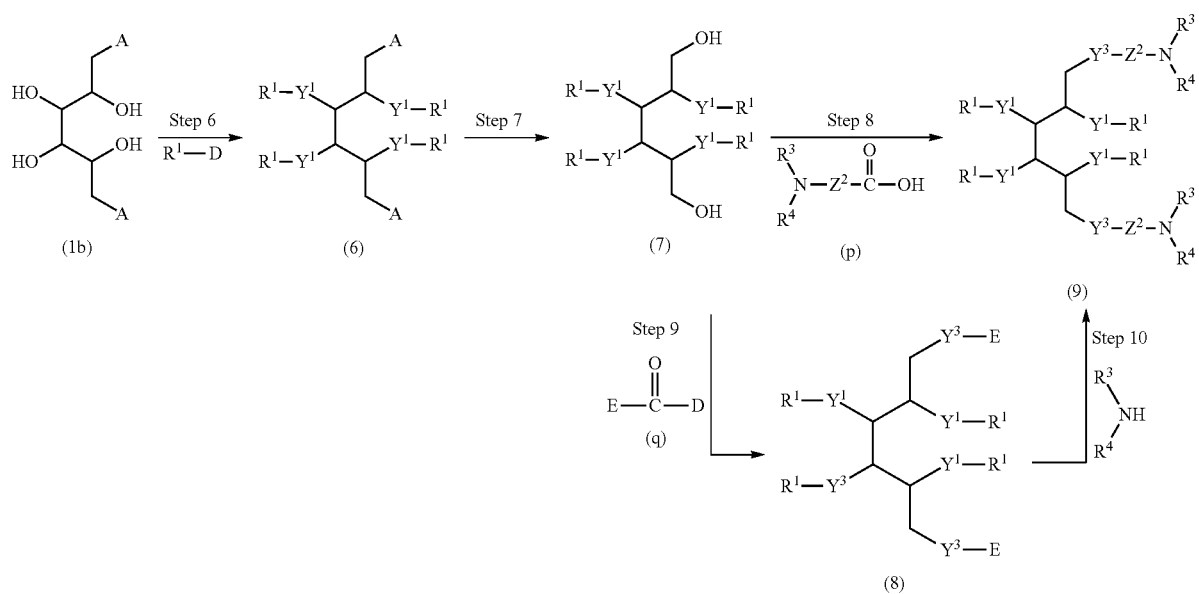

wherein, A is a protecting group (e.g., isopropylidene group, benzylidene group, benzoyl group, benzyl group, trityl group, 4-methoxytrityl group, 4,4'-dimethoxytrityl group, trialkylsilyl group and the like), D is a hydroxyl group or a halogen atom (e.g., iodine atom, bromine atom, chlorine atom and the like), and E is a group represented by the formula (E) or a vinyl group.

$$B-Z^2- \quad (E)$$

wherein $Z^2$ is an alkylene group having 1-6 carbon atoms, and

B is a leaving group (e.g., iodine atom, bromine atom, chlorine atom, methanesulfonyloxy group, p-toluenesulfonyloxy group, trifluoromethanesulfonyloxy group and the like).

Step 6 (Esterification)

A compound represented by the formula (1b) and a compound represented by $R^1$-D wherein $R^1$ and D are as defined above are reacted to give a compound represented by the formula (6).

When D in $R^1$-D is a hydroxyl group, a condensing agent such as DCC, DIC, EDC and the like is used for the reaction. The amount thereof to be used is generally 4-10 molar equivalents, preferably 5-8 molar equivalents, relative to a compound represented by the formula (1b).

A base catalyst is added for the reaction. As the base catalyst, DMAP, pyridine, triethylamine and the like can be mentioned, and DMAP is preferable.

A solvent is used for the reaction. The solvent is not particularly limited as long as it does not inhibit the reaction, and can dissolve the substrate. Specifically, chloroform, dichloromethane, toluene, ethyl acetate and the like can be mentioned, and chloroform is preferable.

The reaction temperature is generally 0-60° C., preferably 10-40° C. The reaction time is generally 1-50 hr, preferably 10-30 hr.

The obtained compound represented by the formula (6) can be appropriately purified by means such as extraction, recrystallization, adsorption treatment, reprecipitation, column chromatography and the like.

Step 7 (Deprotection)

A protecting group of the compound represented by the formula (6) is removed to give a compound represented by the formula (7) containing two free hydroxyl groups.

When A is a trialkylsilyl group, fluoride is used for the reaction. As the fluoride, tetrabutylammonium fluoride, tetrapropylammonium fluoride, tetraethylammonium fluoride, tetramethylammonium fluoride, hydrofluoric acid, cesium fluoride and the like can be mentioned, and tetrabutylammonium fluoride is preferable.

The amount of fluoride to be used is generally 2-10 molar equivalents, preferably 4-8 molar equivalents, relative to a compound represented by the formula (6).

In the process of deprotection of trialkylsilyl group, a strong base, alkoxide, is produced. Since decomposition and transfer of ester occurs in the presence of alkoxide, rapid neutralization is necessary. Therefore, an acid to be a proton source is preferably added to the reaction system. When the acid is too strong, it decomposes ester. Thus, a weak acid is preferable. Specifically, acetic acid, oxalic acid, citric acid, phosphoric acid, benzoic acid, boric acid, trimethylamine hydrochloride and the like can be mentioned, and acetic acid is preferable.

The amount of acid to be used is generally 2-10 molar equivalents, preferably 4-8 equivalents, relative to a compound represented by the formula (6).

A solvent is used for the reaction. As the solvent, tetrahydrofuran, chloroform, ethyl acetate, ethanol, methanol and the like can be mentioned, and tetrahydrofuran is preferable.

The reaction temperature is generally 0-70° C., preferably 10-60° C. The reaction time is generally 1-12 hr, preferably 4-8 hr.

The obtained compound represented by the formula (7) can be appropriately purified by means such as extraction, recrystallization, adsorption treatment, reprecipitation, column chromatography and the like.

Step 8 (Esterification)

A compound represented by the formula (7) and a compound represented by the formula (p) wherein $R^3$, $R^4$ and $Z^2$ are as defined above are reacted to give a compound represented by the formula (9) of the present invention.

A condensing agent such as DCC, DIC, EDC and the like is used for the reaction. During reaction, a compound represented by the formula (7) and a compound represented by the formula (p) may be directly reacted, or an acid anhydride of a compound represented by the formula (p) may be formed and reacted with a compound represented by the formula (7).

A base catalyst is added for the reaction. As the base catalyst, DMAP, pyridine, triethylamine and the like can be mentioned, and DMAP is preferable.

The amount of a compound represented by the formula (p) to be charged is generally 2-10 molar equivalents, preferably 4-8 molar equivalents, relative to a compound represented by the formula (7).

While a solvent may be used for the reaction or the reaction may be performed without solvent, since a compound represented by the formula (p) is a highly-polar solid, and needs to be dispersed in the reaction system, a solvent is preferably used. As the solvent that disperses a compound represented by the formula (p), for example, chloroform, dichloromethane, toluene, ethyl acetate and the like can be mentioned. Of these, chloroform is preferable.

The reaction temperature is generally 10-60° C., preferably 20-40° C. The reaction time is generally 1-20 hr, preferably 2-10 hr.

The obtained compound represented by the formula (9) can be appropriately purified by means such as extraction, recrystallization, adsorption treatment, reprecipitation, column chromatography and the like.

Step 9 (Esterification)

A compound represented by the formula (7) and a compound represented by the formula (q) (wherein D and E are as defined above) are reacted to give a compound represented by the formula (8).

When D in a compound represented by the formula (q) is a hydroxyl group, a condensing agent such as DCC, DIC, EDC and the like is used for the reaction. A compound represented by the formula (7) and a compound represented by the formula (q) may be directly reacted, or an acid anhydride of a compound represented by the formula (q) may be formed and reacted with a compound represented by the formula (7).

A base catalyst is added for the reaction. As the base catalyst, DMAP, pyridine, triethylamine and the like can be mentioned, and DMAP is preferable.

When D in a compound represented by the formula (q) is a halogen atom, a base is added to neutralize halogenated hydrogen to be by-produced. As the base, triethylamine, pyridine and the like can be mentioned.

A solvent is used for the reaction. As the solvent, chloroform, dichloromethane, toluene, ethyl acetate and the like can be mentioned, and toluene is preferable.

The amount of a compound represented by the formula (q) to be charged is generally 2-10 molar equivalents, preferably 2-5 molar equivalents, relative to a compound represented by the formula (7).

The reaction temperature is generally 0-60° C., preferably 10-40° C., the reaction time is generally 1-10 hr, preferably 1-5 hr.

The obtained compound represented by the formula (8) can be appropriately purified by means such as extraction, recrystallization, adsorption treatment, reprecipitation, column chromatography and the like.

Step 10 (Amination)

A secondary amine containing $R^3$ and $R^4$ and a compound represented by the formula (8) are reacted to give a compound represented by the formula (9) of the present invention.

For the reaction, a base catalyst such as potassium carbonate, sodium carbonate, potassium t-butoxide and the like may be used, or the reaction may be performed without catalyst.

A solvent may be used for the reaction or the reaction may be performed without solvent. As the solvent, for example, ethyl acetate, dichloromethane, chloroform, benzene, toluene, THF and the like can be used. Of these, toluene is preferably used.

The amount of secondary amine containing $R^3$ and $R^4$ to be charged is generally 1-20 molar equivalents, preferably 5-10 molar equivalents relative to a compound represented by the formula (8).

The reaction temperature is generally 10-100° C., preferably 60-80° C. The reaction time is generally 1-10 hr, preferably 2-6 hr.

The obtained compound represented by the formula (9) can be appropriately purified by means such as extraction, recrystallization, adsorption treatment, reprecipitation, column chromatography and the like.

Those of ordinary skill in the art can produce a desired cationic lipid d of the present invention by appropriately selecting the starting material and performing the reactions according to the method of the Examples in the present specification.

2. Lipid Membrane Structure of the Present Invention

The lipid membrane structure of the present invention is now explained. The lipid membrane structure of the present invention contains a cationic lipid represented by the above-mentioned formula (1) (i.e., the cationic lipid of the present invention) as a membrane-constituting lipid. Here, the "lipid membrane structure" in the present invention means a lipid membrane structure wherein the hydrophilic groups of the membrane-constituting lipid are arranged in the interface, facing the aqueous phase side.

While the form of the lipid membrane structure of the present invention is not particularly limited, for example, liposome (e.g., monolayer liposome, multilayer liposome etc.), O/W emulsion, W/O/W emulsion, spherical micelle, worm-like micelle, or unspecified layer structure and the like can be mentioned as a form of dispersion of the cationic lipid of the present invention in an aqueous solvent. The form of the lipid membrane structure of the present invention is preferably a liposome.

The lipid membrane structure of the present invention may further contain, in addition to the cationic lipid of the present invention, other constituent components other than the cationic lipid. Examples of such other constituent component include lipid (e.g., phospholipid (e.g., phosphatidylethanolamine, phosphatidylinositol, phosphatidylserine, phosphatidic acid, phosphatidylglycerol, phosphatidylcholine etc.), glycolipid, peptidelipid, cholesterol, cationic lipid other than the cationic lipid of the present invention, PEG lipid etc.), surfactant (e.g., CHAPS, sodium cholate salt, octylglycoside, N-D-gluco-N-methylalkanamides, Poloxamers, polyoxyethylene sorbitan fatty acid esters etc.), PEG, protein and the like can be mentioned. The content of other constituent component in the lipid membrane structure of the present invention is generally 5-90 wt %, preferably 10-30 wt %.

The lipid membrane structure of the present invention may contain only one kind of the cationic lipid of the present invention or two or more kinds in combination. Using two or more kinds of the cationic lipid of the present invention, pKa of the lipid membrane structure of the present invention can be freely adjusted within the range of 4-7. By adjusting the pKa of the lipid membrane structure of the present invention to a value suitable for the object, a functional nucleic acid can be intracellularly delivered highly efficiently.

While the content of the lipid membrane structure of the present invention to be contained in the lipid membrane structure of the present invention is not particularly limited, for example, when the lipid membrane structure of the present invention is used for the below-mentioned nucleic acid-introducing agent, it is preferable that the lipid membrane structure of the present invention contain the cationic lipid of the present invention in an amount sufficient for introducing the nucleic acid. The content of the cationic lipid of the present invention in the lipid membrane structure of the present invention is generally 5-100 mol %, preferably 30-90 mol %, more preferably 50-70 mol %, of the total lipid amount contained in the lipid membrane structure of the present invention.

The lipid membrane structure of the present invention can be prepared by dissolving or dispersing the cationic lipid of the present invention and other constituent components (lipid etc.) in a suitable solvent or dispersing medium, for example, aqueous solvent and alcoholic solvent, and performing an operation to induce organization as necessary.

Examples of the "operation to induce organization" include methods known per se such as an ethanol dilution method, a simple hydration method, sonication, heating, vortex, an ether injecting method, a French press method, a cholic acid method, a $Ca^{2+}$ fusion method, a freeze-thaw method, a reversed-phase evaporation method and the like.

3. Nucleic Acid-Introducing Agent of the Present Invention

By introducing a nucleic acid into a lipid membrane structure containing the cationic lipid of the present invention and bringing same into contact with cells in vivo and/or ex vivo, the nucleic acid can be introduced into the cell. Therefore, the present invention also provides a nucleic acid-introducing agent (hereinafter to be referred to as "agent of the present invention").

The agent of the present invention is mainly characterized in that it contains the aforementioned lipid membrane structure containing cationic lipid of the present invention, and a nucleic acid.

In one embodiment, the agent of the present invention may contain the lipid membrane structure of the present invention and a nucleic acid. In this case, the nucleic acid is preferably introduced into the lipid membrane structure of the present invention. As used herein, a nucleic acid being "introduced" into the lipid membrane structure of the present invention means encapsulating the nucleic acid in a space formed by a lipid bilayer membrane.

The nucleic acid that can be introduced into the lipid membrane structure of the present invention is not particularly limited, and any nucleic acid can be used. Examples of the kind of nucleic acid include, but are not limited to, DNA, RNA, chimera nucleic acid of DNA and RNA, DNA/RNA hybrid and the like. While any nucleic acid having 1 to 3 chains can be used, it is preferably a single strand or double strand. The nucleic acid may be other type of nucleotide such as N-glycoside of purine or pyrimidine base or other oligomer having a non-nucleotide backbone (e.g., commercially available peptide nucleic acid (PNA) etc.), other oligomer containing a special bond (said oligomer comprising base pairing or a nucleotide having a configuration permitting attachment of base, which are found in DNA and RNA) and the like. Furthermore, it may be a nucleic acid added with known modification, for example, nucleic acid with a label known in the field, nucleic acid with a cap, methylated nucleic acid, one or more natural nucleotides substituted by an analog, nucleic acid with intramolecular nucleotidyl modification, nucleic acid with non-charge bond (e.g., methylphosphonate, phosphotriester, phosphoramidate, carbamate and the like), nucleic acid with a charged bond or sulfur-containing bond (e.g., phosphorothioate, phosphorodithioate and the like), nucleic acid with a side chain group such as protein (nuclease, nuclease inhibitor, toxin, antibody, signal peptide, poly-L-lysine and the like), sugar (e.g., monosaccharide and the like) and the like, nucleic acid with an intercalating compound (e.g., acridine, psoralen and the like), nucleic acid with a chelate compound (e.g., metal, radioactive metal, boron, oxidative metal and the like), nucleic acid containing an alkylating agent, or nucleic acid with a modified bond (e.g., a anomer-type nucleic acid and the like).

The kind of DNA that can be used in the present invention is not particularly limited, and can be selected as appropriate according to the object of use. For example, plasmid DNA, cDNA, antisense DNA, chromosomal DNA, PAC, BAC and the like can be mentioned. Preferred are plasmid DNA, cDNA and antisense DNA, and more preferred is plasmid DNA. A circular DNA such as plasmid DNA and the like can be digested as appropriate with a restriction enzyme and the like, and also used as a linear DNA.

The kind of RNA that can be used in the present invention is not particularly limited, and can be selected as appropriate according to the object of use. For example, siRNA, miRNA, shRNA, antisense RNA, messenger RNA (mRNA), single strand RNA genome, double strand RNA genome, RNA replicon, transfer RNA, ribosomal RNA and the like can be mentioned, with preference given to siRNA, miRNA, shRNA, mRNA, antisense RNA, and RNA replicon.

The nucleic acid used in the present invention is preferably purified by a method generally used by those of ordinary skill in the art.

The agent of the present invention can be administered into the body (in vivo) for the purpose of, for example, prophylaxis and/or treatment of a disease. Therefore, the nucleic acid to be used in the present invention preferably has a prophylactic and/or therapeutic activity for a given disease (nucleic acid for prophylaxis or treatment). Examples of such nucleic acid include nucleic acid and the like used for, so-called gene therapy.

While the method of introducing a nucleic acid into the lipid membrane structure of the present invention is not particularly limited, the nucleic acid can be introduced into the lipid structure of the present invention by, for example, achieving coexistence of constituent components of the lipid membrane structure of the present invention and a desired nucleic acid during formation of the lipid membrane structure of the present invention. For example, when the lipid membrane structure of the present invention is formed by an ethanol dilution method, an aqueous nucleic acid solution and a solution of the constituent components (lipid etc.) of the lipid membrane structure of the present invention in an ethanol are vigorously stirred in a vortex and the like, and the mixture is diluted with an appropriate buffer, whereby a suspension of the lipid membrane structure of the present invention introduced with the nucleic acid is obtained. When the lipid membrane structure of the present invention is formed by a simple hydration method, the constituent components (lipid etc.) of the lipid membrane structure of the present invention are dissolved in an appropriate organic solvent, and the solution is placed in a glass container and dried under reduced pressure to evaporate the solvent, whereby a lipid thin film is obtained. Thereto is added an aqueous nucleic acid solution and, after hydration, the mixture is sonicated by a sonicator, whereby a suspension of the lipid membrane structure of the present invention introduced with the nucleic acid is obtained.

As one form of the agent of the present invention, for example, a multifunctional envelope-type nano device (hereinafter to be referred to as MEND) can be mentioned. The MEND can be prepared by, for example, introducing an electrostatic complex of a nucleic acid and a polycation (e.g., protamine etc.) into the lipid membrane structure of the present invention and the like (Kogure K et al., Multifunctional envelope-type nano device (MEND) as a non-viral gene delivery system. Adv. Drug Deliv. Rev., 60, 559-571 (1 Mar. 2008). This structure (MEND) can be used as a drug delivery system for selectively delivering a nucleic acid and the like into a particular cell, and useful for, for example, a DNA vaccine, gene therapy of tumor and the like, by introducing antigen gene into dendritic cells.

The surface charge (zeta potential) of the lipid membrane structure of the present invention introduced with the nucleic acid is preferably −10 to +10 mV, more preferably −10 to +5 mV. In conventional transgene, particles electrically charged to have a plus surface potential have been mainly used. This is useful as a method for promoting electrostatic interactions with heparin sulfate on the negatively-charged cell surface to enhance uptake into cells. However, positive surface charge may induce suppression of transcription due to the intracellular interaction with the introduced gene and suppression of translation due to the intracellular interaction with mRNA. This problem can be solved by adjusting the surface charge to fall within the above-mentioned range. The surface charge can be measured using Metasizer Nano (Malvern instruments Ltd.). The surface charge can be adjusted to a desired value by appropriately adjusting the composition of the constituent components of the lipid membrane structure of the present invention within the range not impairing the object of the present invention.

The nucleic acid contained in the agent of the present invention can be introduced into a cell by contacting the agent of the present invention with the cell. The kind of the "cell" is not particularly limited, a prokaryotic or eucaryotic cell can be used, with preference given to an eucaryotic cell. The kind of the eukaryotic cell is not particularly limited and, for example, vertebrates such as mammals including human (e.g., human, monkey, mouse, rat, hamster, bovine etc.), birds (e.g., chicken, ostrich etc.), *amphibia* (e.g., frog etc.), fishes (e.g., zebrafish, rice-fish etc.) and the like; invertebrates such as insects (e.g., silk moth, moth, *Drosophila* etc.) and the like; plants; microorganisms (e.g., yeasts etc.), and the like can be mentioned. More preferably, the target cell in the present invention is preferably an animal (e.g., vertebrate cell etc.) or plant cell, more preferably a mammalian cell. The cell may be a culture cell line including a cancer cell, or a cell isolated from an individual or tissue, or a cell of a tissue or tissue piece. The cell may be an adherent cell or a non-adherent cell.

A method of contacting the agent of the present invention with the cell in vitro is specifically explained below.

The cells are suspended in a suitable medium several days before contact with the agent of the present invention, and cultured under appropriate conditions. At the time of contact with the agent of the present invention, the cells may or may not be in a proliferative phase.

The culture medium on contact may be a serum-containing medium or a serum-free medium, wherein the serum concentration of the medium is preferably not more than 30 wt %, more preferably not more than 20 wt %, since when the medium contains excess protein such as serum and the like, the contact between the agent of the present invention and the cell may be inhibited.

The cell density on contact is not particularly limited, and can be appropriately determined in consideration of the kind of the cell and the like. It is generally within the range of $1\times10^4$-$1\times10^7$ cells/mL.

For example, a suspension of the lipid membrane structure of the present invention introduced with the aforementioned nucleic acid is added to the thus-prepared cells. The amount of the suspension to be added is not particularly limited, and can be appropriately determined in consideration of the cell number and the like. The concentration of the lipid membrane structure of the present invention in the suspension to be contacted with the cells is not particularly limited as long as the desired introduction of the nucleic acid into the cells can be achieved. The lipid concentration is generally 1-100 nmol/ml, preferably 10-50 nmol/ml, and the concentration of the nucleic acid is generally 0.01-100 μg/ml, preferably 0.1-10 μg/ml.

After addition of the aforementioned suspension to the cells, the cells are cultivated. The temperature, humidity, $CO_2$ concentration and the like during the culture can be appropriately determined in consideration of the kind of the cell. When the cell is derived from a mammal, temperature about 37° C., humidity about 95% and $CO_2$ concentration about 5% are generally employed. While the culture period can also be appropriately determined in consideration of the conditions such as the kind of the cell and the like, it is generally 0.1—for 24 hr, preferably 0.25—for 4 hr, more preferably 0.5—for 2 hr. When the above-mentioned culture time is too short, the nucleic acid is not sufficiently introduced into the cells, and when the culture time is too long, the cells may become weak.

By the above-mentioned culture, the nucleic acid is introduced into cells. The culture is further continued preferably by exchanging the medium with a fresh medium, or adding a fresh medium to the medium. When the cell is a mammal-derived cell, the fresh medium preferably contains a serum or nutrition factor.

As mentioned above, a nucleic acid can be introduced into cells not only outside the body (in vitro) but also in the body (in vivo) by using the agent of the present invention. That is, by administration of the agent of the present invention to a subject, the lipid membrane structure of the present invention introduced with the nucleic acid reaches and contacts with the target cells, and the nucleic acid introduced into the lipid membrane structure is introduced into the cells in vivo. The subject to which the agent of the present invention can be administered is not particularly limited and, for example, vertebrates such as mammals including human (e.g., human, monkey, mouse, rat, hamster, bovine etc.), birds (e.g., chicken, ostrich etc.), *amphibia* (e.g., frog etc.), fishes (e.g., zebrafish, rice-fish etc.) and the like, invertebrates such as insects (e.g., silk moth, moth, *Drosophila* etc.) and the like, plants and the like can be mentioned. The subject of administration of the agent of the present invention is preferably human or other mammal.

The kind of the target cell is not particularly limited, and a nucleic acid can be introduced into cells in various tissues (e.g., liver, kidney, pancreas, lung, spleen, heart, blood, muscle, bone, brain, stomach, small intestine, large intestine, skin, adipose tissue etc.) by using the agent of the present invention.

In addition, the lipid membrane structure contained in the agent of the present invention may be introduced with a compound other than a nucleic acid. When the agent of the present invention contains a lipid membrane structure introduced with a compound other than a nucleic acid, the method of administering the agent of the present invention to a subject (e.g., vertebrate, invertebrate, etc.) is not particularly limited as long as the lipid membrane structure reaches and contacts the target cell and the compound introduced into the lipid membrane structure can be introduced into the cell, and an administration method known per se (e.g., oral administration, parenteral administration (e.g., intravenous administration, intramuscular administration, topical administration, transdermal administration, subcutaneous administration, intraperitoneal administration, spray etc.) etc.) can be appropriately selected in consideration of the kind of the compound to be introduced, the kind and the site of the target cell and the like. The dose of the agent of the present invention is not particularly limited as long as the introduction of the compound into the cells can be achieved, and can be appropriately selected in consideration of the kind of the subject of administration, administration method, the kind of the compound to be introduced, the kind and the site of the target cell and the like. The method of introducing the compound into the lipid membrane structure of the present invention is not particularly limited and, for example, a method similar to the aforementioned method of introducing a nucleic acid into the lipid membrane structure of the present invention or a method analogous thereto can be used for the production.

While the dosage form of the agent of the present invention is not particularly limited, for example, injection (e.g., subcutaneous injection, intravenous injection, intramuscular injection, intraperitoneal injection, drip infusion etc.) and the like can be mentioned.

The agent of the present invention can be produced by formulating the lipid membrane structure of the present invention by a conventional means according to the use (e.g., reagent for studies, medicament etc.).

When the agent of the present invention is provide as a reagent for studies, the agent of the present invention can be provide using the lipid membrane structure of the present invention as it is or a sterile solution or suspension with, for example, water or other physiologically acceptable solution (e.g., aqueous solvent (e.g., malic acid buffer etc.), organic solvent (e.g., methanol, ethanol, DMSO and the like) or a mixture of aqueous solvent and organic solvent etc.). The agent of the present invention can appropriately contain physiologically acceptable additive known per se (e.g., excipient, vehicle, preservative, stabilizer, binder and the like).

When the agent of the present invention is provided as a medicament, the agent of the present invention can be provided as an oral preparation (e.g., tablet, capsule etc.) or parenteral agent (e.g., injection, spray etc.), preferably parenteral agent (more preferably, injection), by using the lipid membrane structure of the present invention as it is or by blending the lipid membrane structure with a pharmaceutically acceptable known additives such as carrier, flavor, excipient, vehicle, preservative, stabilizer, binder and the like in a unit dosage form required for practicing conventionally admitted preparation formulation.

The agent of the present invention can also be formulated as a preparation for children as well as for adults.

The agent of the present invention can also be provided in the form of a kit. The kit can contain, in addition to the lipid membrane structure of the present invention and a nucleic acid, a reagent used for the introduction of a nucleic acid into the cell. In one embodiment, the agent (or kit) of the present invention can further contain a polycation (e.g., protamine etc.). The agent (or kit) of the present invention further containing polycation (e.g., protamine etc.) can easily introduce an electrostatic complex of nucleic acid and polycation (e.g., protamine etc.) into the lipid membrane structure of the present invention to prepare MEND. The MEND can be utilized for the intracellular introduction of a nucleic acid.

EXAMPLES

The present invention is explained in detail in the following by referring to Examples; however, the present invention is not limited by the Examples in any manner.

The abbreviations used in the explanation of the Examples each mean the following.

Lin-Ms: linoleyl-methanesulfonate
MIM: 3,4-O-isopropylidene-D-mannitol
TLMIM: 1,2,5,6-tetralinoleyl-3,4-O-isopropylidene-D-mannitol
TLM: 1,2,5,6-tetralinoleyl-D-mannitol
TLM-C2-Br: 1,2,5,6-tetralinoleyl-3,4-di(bromoacetyl)-D-mannitol
DMAP: 4-dimethylaminopyridine
Chol: cholesterol
PEG2000-DMG: 1,2-dimyristoyl-sn-glycerol, methoxypolyethylene glycol (PEG molecular weight: 2000) Decenyl-Ms: decenyl methanesulfonate
TDMIM: 1,2,5,6-tetrakis(decenyl)-3,4-O-isopropylidene-D-mannitol
TDM: 1,2,5,6-tetrakis(decenyl)-D-mannitol
TBDPS-Cl: tert-butyldiphenylchlorosilane
DIPEA: diisopropylethylamine
DTBDPS-M: 1,6-di-(tert-butyldiphenylsilyl)-D-mannitol
DTBDPS-TLMES: 1,6-di-(tert-butyldiphenylsilyl)-2,3,4,5-tetralinoleoyl-D-mannitol
TLMES: tetralinoleoyl-D-mannitol
TBAF: tetrabutylammonium fluoride Table 2 and Table 3 show the names and structures of the cationic lipids produced in the following Examples and Comparative Examples.

TABLE 2
| | name of cationic lipid | structure |
|---|---|---|
| Ex. 1 | TLM-C2-DMA | 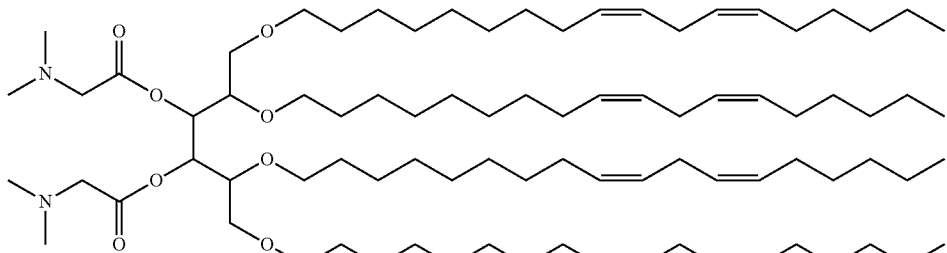 |
| Ex. 2 | TLM-C3-DMA | 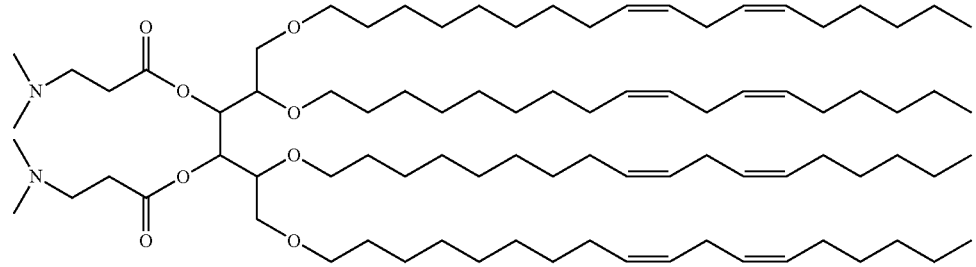 [SMILES: CCCCC/C=C\C/C=C\CCCCCCCCOCC(OCCCCCCCC/C=C\C/C=C\CCCCC)C(OC(=O)CCN(C)C)C(OC(=O)CCN(C)C)C(COCCCCCCCC/C=C\C/C=C\CCCCC)OCCCCCCCC/C=C\C/C=C\CCCCC] |
| Ex. 3 | TLM-C4-DMA | 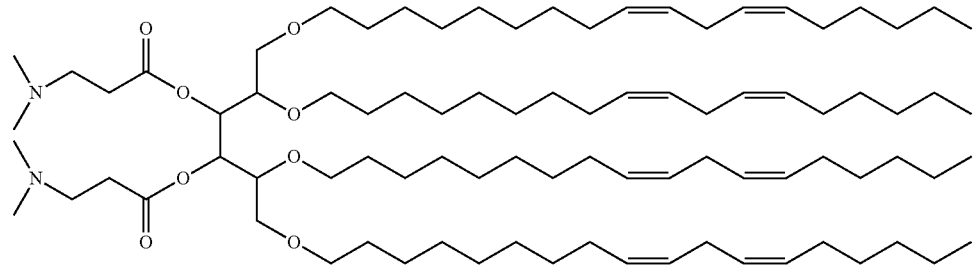 [SMILES: CCCCC/C=C\C/C=C\CCCCCCCCOCC(OCCCCCCCC/C=C\C/C=C\CCCCC)C(OC(=O)CCN(C)C)C(OC(=O)CCN(C)C)C(COCCCCCCCC/C=C\C/C=C\CCCCC)OCCCCCCCC/C=C\C/C=C\CCCCC] |
| Ex. 4 | TDM-C3-DMA | 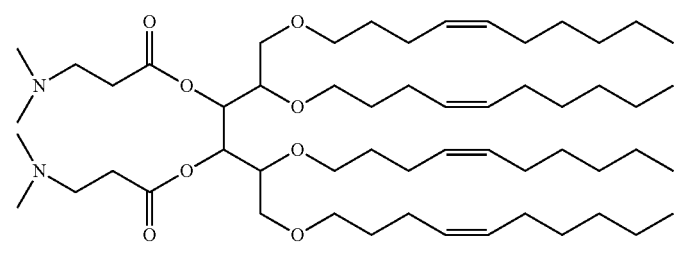 [SMILES: CCCCC/C=C\CCCOCC(OCCC/C=C\CCCCC)C(OC(=O)CCN(C)C)C(OC(=O)CCN(C)C)C(COCCC/C=C\CCCCC)OCCC/C=C\CCCCC] |
| Ex. 5 | TLMES-C3-DMA | 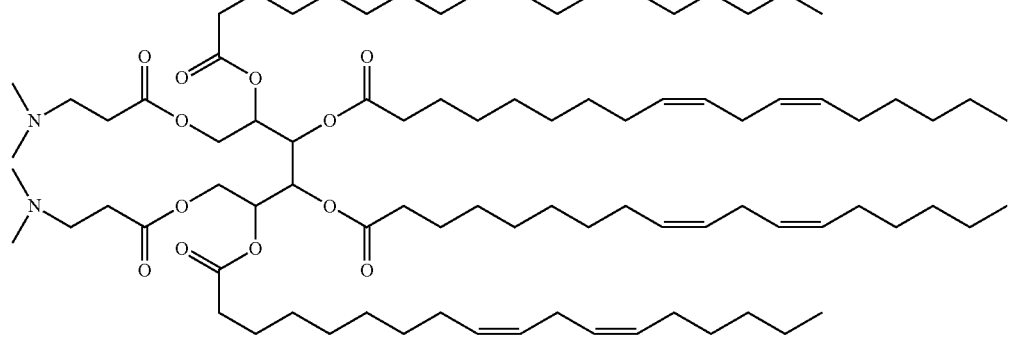 |

TABLE 3

| name of cationic lipid | structure |
|---|---|
| Comp. Ex. 1  DLinDAP | (structure shown) |
| Comp. Ex. 2  DODAP | (structure shown) |

Production Example 1

<Silyl Group Protection> Synthesis of DTBDPS-M

To D-mannitol (manufactured by Tokyo Chemical Industry Co., Ltd.) (3.0 g, 16.5 mmol) were added N,N-dimethylformamide (48 mL) and DIPEA (manufactured by Kanto Chemical Co., Inc.) (6.4 g, 49.4 mmol), and the mixture was cooled to 0-10° C. with stirring. Thereto was added dropwise a solution of TBDPS-Cl (manufactured by Tokyo Chemical Industry Co., Ltd.) (13.6 g, 49.4 mmol) in N,N-dimethylformamide (16 mL) so that the temperature would not exceed 10° C. After the completion of the dropwise addition, the temperature was increased to 20° C. and the mixture was stirred for 2.5 hr. Disappearance of D-mannitol and monosilyl form was confirmed by TLC analysis (eluent: chloroform/methanol=9/1 (v/v), color developed with potassium permanganate), and the reaction was terminated. To the reaction solution were added ion exchange water (120 mL) and toluene (60 mL) and the mixture was stirred at for 10 min and stood for 10 min to allow for layer separation. The obtained toluene layer was washed again with ion exchange water (40 mL) and the toluene layer was concentrated. The obtained concentrate was dissolved in acetonitrile (170 mL) and purified by extracting 5 times with hexane (170 mL). The solvent was evaporated from the obtained acetonitrile layer to give DTBDPS-M (9.2 g).

The obtained DTBDPS-M was analyzed for $^1$H-NMR (600 MHz, CDCl$_3$) and confirmed to be the object product.

δ1.03 ppm (s, 18H, (C$\underline{H}_3$—)$_3$C—), δ3.79-3.89 ppm (m, 8H, —O—C$\underline{H}_2$—CH(—OH)—CH(—OH)—), δ7.25-7.72 ppm (m, 20H, tBu-Si(-P$\underline{h}$)$_2$—)

[Example 1] (Synthesis of TLM-C2-DMA)

<Mesylation> Synthesis of Lin-Ms

Linoleyl alcohol (100 g) (manufactured by NOF CORPORATION, purity≥99%) (0.38 mol) and trimethylamine (manufactured by Kanto Chemical Co., Inc.) (46 g, 0.45 mol) were dissolved in dehydrating toluene (500 g), and cooled to 10° C. with stirring under a nitrogen atmosphere. Methanesulfonyl chloride (manufactured by Kanto Chemical Co., Inc.) (47 g, 0.41 mol) was added dropwise over 2 hr until the temperature became 30° C. or below. After the completion of the dropwise addition, disappearance of the spot of linoleyl alcohol was confirmed by TLC analysis (eluent: chloroform, phosphoric acid-copper sulfate color development). Ethanol (5.2 g, 0.11 mol) was added, and insoluble materials were filtered off using filter paper. The filtrate was washed with ion exchange water (150 g), and the aqueous layer was discarded. The mixture was washed again with water, and the obtained organic layer was subjected to a dehydrating treatment by adding anhydrous magnesium sulfate (20 g). Insoluble materials were filtered off using filter paper, and the solvent in the filtrate was evaporated by an evaporator to give Lin-Ms (120 g).

The obtained Lin-Ms was analyzed for $^1$H-NMR (600 MHz, CDCl$_3$) and confirmed to be the object product.

δ0.89 ppm (t, 3H, C$\underline{H}_3$—CH$_2$—), δ1.41-1.26 ppm (m, 16H, CH$_3$—C$\underline{H}_2$—C$\underline{H}_2$—C$\underline{H}_2$—, —CH=CH—CH$_2$—C$\underline{H}_2$—C$\underline{H}_2$—C$\underline{H}_2$—C$\underline{H}_2$—C$\underline{H}_2$—), δ1.75 ppm (quint, 2H, —C$\underline{H}_2$—CH$_2$—O—), δ2.05 ppm (q, 4H, —C$\underline{H}_2$—CH=CH—CH$_2$—CH=CH—C$\underline{H}_2$—), δ2.77 ppm (t, 2H, —CH=CH—C$\underline{H}_2$—CH=CH—), δ3.00 ppm (s, 3H, —SO$_2$—C$\underline{H}_3$), δ4.22 ppm (t, 2H, —C$\underline{H}_2$—O—), δ5.41-5.31 ppm (m, 4H, —C$\underline{H}$=C$\underline{H}$—CH$_2$—C$\underline{H}$=CH—)

<Etherification> Synthesis of TLMIM

Toluene (40 g) was added to MIM (manufactured by Tokyo Chemical Industry Co., Ltd.) (2.0 g, 9.00 mmol), and potassium hydroxide (manufactured by Kanto Chemical Co., Inc.) (4.2 g, 74.50 mmol) and Lin-Ms (18.6 g, 54.00 mmol) were further added, and the mixture was stirred at 25° C. for 5 min. The mixture was heated to 80° C. and stirred for 14 hr. By $^1$H-NMR analysis, emergence of a peak derived from the reaction product and cease of decrease in the integrated value of the peak derived from Lin-Ms were confirmed and the reaction was discontinued. Toluene (60 mL) and ion exchange water (100 mL) were added to the reaction solution and the mixture was stirred at 20° C. for 10 min and stood for 10 min to allow for layer separation. The aqueous layer was removed, and the mixture was washed again with water. Then, 25 wt % brine (100 mL) was added, the mixture was stirred for 10 min and stood for 10 min to allow for layer separation, and the aqueous layer was removed. The obtained organic layer was subjected to a dehydrating treatment by adding anhydrous magnesium sulfate (2.0 g). Insoluble materials were filtered off using filter paper, and the solvent in the filtrate was evaporated by an evaporator to give a brown liquid (11.5 g).

The obtained brown liquid (10 g) was purified by silica gel column chromatography (eluent: hexane/ethyl acetate=100/0-98/2 (v/v)) to give TLMIM (3.0 g). The obtained TLMIM was analyzed for $^1$H-NMR (600 MHz, CDCl$_3$) and confirmed to be the object product.

δ0.89 ppm (t, 12H, CH$_3$—CH$_2$—), δ1.38-1.29 ppm (m, 64H, CH$_3$—CH$_2$—CH$_2$—CH$_2$—, —CH=CH—CH$_2$—CH$_2$—CH$_2$—CH$_2$—CH$_2$—CH$_2$—), δ1.38 ppm (s, 6H, —O—C(CH$_3$)$_2$—O—), δ1.56 ppm (m, 8H, —CH$_2$—CH$_2$—O—), δ2.05 ppm (q, 16H, —CH$_2$—CH=CH—CH$_2$—CH=CH—CH$_2$—), δ2.77 ppm (t, 8H, —CH=CH—CH$_2$—CH=CH—), δ3.54-3.41 ppm (m, 10H, —CH$_2$—CH$_2$—O—, —O—CH$_2$—CH—CH—O—C(CH$_3$)$_2$—), δ3.67 ppm (m, 4H, —O—CH$_2$—CH—CH—O—C(CH$_3$)$_2$—), δ4.06 ppm (d, 2H, —O—CH$_2$—CH—CH—O—C(CH$_3$)$_2$—), δ5.40-5.31 ppm (m, 16H, —CH=CH—CH$_2$—CH=CH—)

<Deprotection> Synthesis of TLM

To TLMIM (6.7 g, 5.51 mmol) were added ethanol (67 mL), ion exchange water (4.0 g, 220.40 mmol), and hydrochloric acid (4.0 M dioxane solution) (manufactured by Tokyo Chemical Industry Co., Ltd.) (13.8 mL) (55.10 mmol as hydrochloric acid), and the mixture was stirred at 60° C. for 6 hr. Disappearance of the spot of TLMIM was confirmed by TLC analysis (eluent: chloroform/methanol=99.5/0.5 (v/v), phosphoric acid-copper sulfate color development), and the reaction was terminated. The reaction mixture was stood for 13 hr while cooling to 5° C. to allow for layer separation, and the organic layer was recovered. The solvent was evaporated from the recovered organic layer by nitrogen bubbling to give a faint brown liquid (5.1 g).

The obtained faint brown liquid (4.6 g) was purified by silica gel column chromatography (eluent: hexane/ethyl acetate=98/2-9/1 (v/v)) to give TLM (3.5 g).

The obtained TLM was analyzed for $^1$H-NMR (600 MHz, CDCl$_3$) and confirmed to be the object product.

δ0.89 ppm (t, 12H, CH$_3$—CH$_2$—), δ1.38-1.28 ppm (m, 64H, CH$_3$—CH$_2$—CH$_2$—CH$_2$—, —CH=CH—CH$_2$—CH$_2$—CH$_2$—CH$_2$—CH$_2$—CH$_2$—), δ1.56 ppm (m, 8H, CH$_2$—CH$_2$—O—), 2.05 ppm (q, 16H, —CH$_2$—CH=CH—CH$_2$—CH=CH—CH$_2$—), 2.77 ppm (t, 8H, —CH=CH—CH$_2$—CH=CH—), 3.30 ppm (d, 2H, —OH), 3.51-3.42 ppm (m, 6H, —O—CH$_2$—CH—CH—OH, —O—CH$_2$—CH—CH—OH), 3.68-3.52 ppm (m, 8H, —CH$_2$—CH$_2$—O—), 3.82 ppm (d, 2H, —O—CH$_2$—CH—CH—OH), 5.39-5.31 ppm (m, 16H, —CH=CH—CH$_2$—CH=CH—)

<Esterification> Synthesis of TLM-C2-Br

TLM (1.0 g, 0.85 mmol) and bromoacetic acid (manufactured by Tokyo Chemical Industry Co., Ltd.) (354.5 mg, 2.55 mmol) were dissolved in chloroform (10 mL), DMAP (manufactured by Koei Chemical Co., Ltd.) (51.9 mg, 0.43 mmol) and DIC (manufactured by Tokyo Chemical Industry Co., Ltd.) (321.8 mg, 2.55 mmol) were added, and the mixture was stirred at 25° C. for 1 hr. Disappearance of the spot of TLM was confirmed by TLC analysis (eluent: chloroform alone, phosphoric acid-copper sulfate color development). Then, the reaction mixture was washed with ion exchange water (10 mL) and 25 wt % brine (10 mL), and the organic layer was recovered. The recovered organic layer was subjected to a dehydrating treatment by adding anhydrous magnesium sulfate (1.0 g). Insoluble materials were filtered off using filter paper, and the solvent in the filtrate was evaporated by an evaporator to give a faint brown liquid (1.6 g).

The obtained faint brown liquid was purified by silica gel chromatography (eluent: hexane/ethyl acetate=100/0-97/3 (v/v)) to give TLM-C2-Br (980 mg).

The obtained TLM-C2-Br was analyzed for $^1$H-NMR (600 MHz, CDCl$_3$) and confirmed to be the object product.

δ0.89 ppm (t, 12H, CH$_3$—CH$_2$—), 1.38-1.27 ppm (m, 64H, CH$_3$—CH$_2$—CH$_2$—CH$_2$—, —CH=CH—CH$_2$—CH$_2$—CH$_2$—CH$_2$—CH$_2$—CH$_2$—), 1.52 ppm (m, 8H, —CH$_2$—CH$_2$—O—), 2.05 ppm (q, 16H, —CH$_2$—CH=CH—CH$_2$—CH=CH—CH$_2$—), 2.77 ppm (t, 8H, —CH=CH—CH$_2$—CH=CH—), 3.51-3.37 ppm (m, 10H, —CH$_2$—CH$_2$—O—, —O—CH$_2$—CH—CH—O—CO—), 3.60 ppm (m, 4H, —O—CH$_2$—CH—CH—O—CO—), 3.84 ppm (s, 4H, —O—CO—CH$_2$—), 5.40-5.31 ppm (m, 16H, —CH=CH—CH$_2$—CH=CH—), δ5.51 ppm (d, 2H, —O—CH$_2$—CH—CH—O—CO—)

<Amination> Synthesis of TLM-C2-DMA

TLM-C2-Br (300 mg, 0.21 mmol) was dissolved in THF (2.2 mL), dimethylamine (2.0 M THF solution) (manufactured by Tokyo Chemical Industry Co., Ltd.) (846 μL) (1.68 mmol as dimethylamine) was added and the mixture was stirred at 25° C. for 4 hr. Emergence of a spot of the reaction product and disappearance of the spot of TLM-C2-Br as a starting material were confirmed by TLC analysis (eluent: chloroform/methanol=96/4 (v/v), phosphoric acid-copper sulfate color development). To the reaction solution were added chloroform (8 mL) and ion exchange water (10 mL) and the mixture was stirred for 10 min, stood for 10 min to allow for layer separation, and the aqueous layer was removed. The mixture was washed 3 times with ion exchange water (10 mL), washed once with 25 wt % brine (10 mL), and the organic layer was recovered. The recovered organic layer was subjected to a dehydrating treatment by adding anhydrous magnesium sulfate (0.5 g). Insoluble portion was filtered off using filter paper, and the solvent in the filtrate was evaporated by an evaporator to give TLM-C2-DMA (260 mg).

The obtained TLM-C2-DMA was analyzed for $^1$H-NMR (600 MHz, CDCl$_3$) and confirmed to be the object product.

δ0.89 ppm (t, 12H, CH$_3$—CH$_2$—), 1.38-1.27 ppm (m, 64H, CH$_3$—CH$_2$—CH$_2$—CH$_2$—, —CH=CH—CH$_2$—CH$_2$—CH$_2$—CH$_2$—CH$_2$—CH$_2$—), 1.52 ppm (m, 8H, —CH$_2$—CH$_2$—O—), 2.05 ppm (q, 16H, —CH$_2$—CH=CH—CH$_2$—CH=CH—CH$_2$—), 2.35 ppm (s, 12H, —N—(CH$_3$)$_2$), 2.77 ppm (t, 8H, —CH=CH—CH$_2$—CH=CH—), 3.16 ppm (q, 4H, —O—CO—CH$_2$—), 3.49-3.35 ppm (m, 10H, —CH$_2$—CH$_2$—O—, —O—CH$_2$—CH—CH—O—CO—), 3.55 ppm (m, 4H, —O—CH$_2$—CH—CH—O—CO—), 5.40-5.31 ppm (m, 16H, —CH=CH—CH$_2$—CH=CH—), 5.47 ppm (d, 2H, —O—CH$_2$—CH—CH—O—CO—)

[Example 2] (Synthesis of TLM-C3-DMA)

<Esterification>

TLM (1.0 g, 0.85 mmol) and dimethylaminopropionic acid hydrochloride (manufactured by Tokyo Chemical Industry Co., Ltd.) (783.8 mg, 5.10 mmol) were dissolved in chloroform (10 mL), DMAP (51.9 mg, 0.43 mmol) and DCC (manufactured by Tama Kagaku Kogyo Co., Ltd.) (1.1 g, 5.10 mmol) were added and the mixture was stirred at 25±5° C. for 1 hr. Disappearance of the spot of TLM was confirmed by TLC analysis (eluent: chloroform/methanol=85/15 (v/v), phosphoric acid-copper sulfate color development). Insoluble materials in the reaction mixture were filtered off using filter paper, and the obtained filtrate was washed with chloroform (10 mL), ion exchange water (20 mL), and methanol (30 mL), and organic layer was recovered. The organic layer was further washed with ion exchange water (20 mL) and methanol (40 mL), and the organic layer was recovered. The recovered organic layer was subjected to a dehydrating treatment by adding anhydrous magnesium sulfate (1.0 g). Insoluble portion was filtered off using filter paper, and the solvent in the filtrate was evaporated by an evaporator to give a faint brown liquid (1.6 g).

The obtained faint brown liquid was purified by silica gel chromatography (eluent: chloroform/methanol=98/2-96/4 (v/v)) to give TLM-C3-DMA (102 mg).

The obtained TLM-C3-DMA was analyzed for $^1$H-NMR (600 MHz, CDCl$_3$) and confirmed to be the object product.

$\delta$0.89 (t, 12H, C$\underline{H}_3$—CH$_2$—), $\delta$1.38-1.27 (m, 64H, CH$_3$—C$\underline{H}_2$—C$\underline{H}_2$—C$\underline{H}_2$—, —CH=CH—CH$_2$—C$\underline{H}_2$—C$\underline{H}_2$—C$\underline{H}_2$—C$\underline{H}_2$—C$\underline{H}_2$—), $\delta$1.52 (m, 8H, —C$\underline{H}_2$—CH$_2$—O—), $\delta$2.05 (q, 16H, —C$\underline{H}_2$—CH=CH—CH$_2$—CH=CH—C$\underline{H}_2$—), $\delta$2.23 (s, 12H, —N—(C$\underline{H}_3$)$_2$), $\delta$2.49 (t, 4H, —O—CO—C$\underline{H}_2$—CH$_2$—), $\delta$2.60 (m, 4H, —O—CO—CH$_2$—C$\underline{H}_2$—), $\delta$2.77 (t, 8H, —CH=CH—C$\underline{H}_2$—CH=CH—), $\delta$3.43 (m, 8H, —CH$_2$—C$\underline{H}_2$—O—), $\delta$3.53 (m, 6H, —O—C$\underline{H}_2$—CH—CH—O—CO—, —O—CH$_2$—C$\underline{H}$—CH—O—CO—), $\delta$5.39-5.30 (m, 18H, —C$\underline{H}$=C$\underline{H}$—CH$_2$—C$\underline{H}$=C$\underline{H}$—, —O—CH$_2$—CH—C$\underline{H}$—O—CO—)

[Example 3] (Synthesis of TLM-C4-DMA)

<Esterification>

TLM (0.5 g, 0.43 mmol) and dimethylaminobutyric acid hydrochloride (ACROS ORGANICS; manufactured by Thermo Fisher Scientific) (427.6 mg, 2.55 mmol) were dissolved in chloroform (5 mL), DMAP (51.9 mg, 0.43 mmol) and DIC (321.8 mg, 2.55 mmol) were added, and the mixture was stirred at 25° C. for 4 hr. Disappearance of the spot of TLM was confirmed by TLC analysis (eluent: chloroform/methanol=85/15 (v/v), phosphoric acid-copper sulfate color development). Then, the reaction mixture was washed with ion exchange water (5 mL) and ethanol (5 mL), and the organic layer was recovered. Similar washing was performed again, and the recovered organic layer was subjected to a dehydrating treatment by adding anhydrous magnesium sulfate (0.5 g). Insoluble portion was filtered off using filter paper, and the solvent in the filtrate was evaporated by an evaporator to give a faint brown liquid (515.8 mg).

400 mg from the obtained faint brown liquid was purified by silica gel chromatography (eluent: chloroform/methanol=96/4-8/2 (v/v)) to give TLM-C4-DMA (244 mg).

The obtained TLM-C4-DMA was analyzed for $^1$H-NMR (600 MHz, CDCl$_3$) and confirmed to be the object product.

$\delta$0.89 ppm (t, 12H, C$\underline{H}_3$—CH$_2$—), $\delta$1.38-1.27 ppm (m, 64H, CH$_3$—C$\underline{H}_2$—C$\underline{H}_2$—C$\underline{H}_2$—, —CH=CH—CH$_2$—C$\underline{H}_2$—C$\underline{H}_2$—C$\underline{H}_2$—C$\underline{H}_2$—), $\delta$1.53 ppm (m, 8H, —C$\underline{H}_2$—CH$_2$—O—), $\delta$1.77 ppm (quint, 4H, —CH$_2$—C$\underline{H}_2$—CH$_2$—N(CH$_3$)$_2$), $\delta$2.05 ppm (q, 16H, —C$\underline{H}_2$—CH=CH—CH$_2$—CH=CH—C$\underline{H}_2$—), $\delta$2.21 ppm (s, 12H, —N—(C$\underline{H}_3$)$_2$), $\delta$2.28 ppm (t, 4H, —C$\underline{H}_2$—CH$_2$—N(CH$_3$)$_2$), $\delta$2.34 ppm (m, 4H, —CH$_2$—CH$_2$—C$\underline{H}_2$—N(CH$_3$)$_2$), $\delta$2.77 ppm (t, 8H, —CH=CH—C$\underline{H}_2$—CH=CH—), $\delta$3.54-3.38 ppm (m, 14H, CH$_2$—C$\underline{H}_2$—O—, —C$\underline{H}_2$—CH—CH—O—CO—, —CH$_2$—C$\underline{H}$—CH—O—CO—), $\delta$5.40-5.32 ppm (m, 18H, —C$\underline{H}$=C$\underline{H}$—CH$_2$—C$\underline{H}$=C$\underline{H}$—, —CH$_2$—CH—C$\underline{H}$—O—CO—)

[Example 4] (Synthesis of TDM-C3-DMA)

<Mesylation> Synthesis of Decenyl-Ms

Decenyl alcohol (manufactured by ALDRICH) (10.0 g, 64.0 mol) and triethylamine (7.8 g, 76.8 mol) were dissolved in dehydrating toluene (50 g), and cooled to 10° C. with stirring under a nitrogen atmosphere. Methanesulfonyl chloride (8.1 g, 70.4 mol) was added dropwise over 30 min until the temperature became 30° C. or below. After the completion of the dropwise addition, disappearance of the spot of decenyl alcohol was confirmed by TLC analysis (eluent: chloroform, phosphoric acid-copper sulfate color development). Ethanol (0.9 g, 19.2 mol) was added, and insoluble materials were filtered off using filter paper. The filtrate was washed with ion exchange water (20 g), and the aqueous layer was discarded. The mixture was washed again with water, and the obtained organic layer was subjected to a dehydrating treatment by adding anhydrous magnesium sulfate (5 g). Insoluble materials were filtered off using filter paper, and the solvent in the filtrate was evaporated by an evaporator to give Decenyl-Ms (14.5 g).

The obtained Decenyl-Ms was analyzed for $^1$H-NMR (600 MHz, CDCl$_3$) and confirmed to be the object product.

$\delta$0.89 ppm (t, 3H, C$\underline{H}_3$—CH$_2$—), $\delta$1.26-1.36 ppm (m, 6H, CH$_3$—C$\underline{H}_2$—C$\underline{H}_2$—C$\underline{H}_2$—), $\delta$1.81 ppm (quint, 2H, —C$\underline{H}_2$—CH$_2$—O—), $\delta$2.02 ppm (q, 2H, CH$_3$—CH$_2$—CH$_2$—C$\underline{H}_2$—CH=), $\delta$2.16 ppm (q, 2H, =CH—C$\underline{H}_2$—CH$_2$—CH$_2$—O—), $\delta$3.00 ppm (s, 3H, —SO$_2$—C$\underline{H}_3$), $\delta$4.23 ppm (t, 2H, —C$\underline{H}_2$—O—), $\delta$5.32 ppm, $\delta$5.45 ppm (q, 2H, —C$\underline{H}$=C$\underline{H}$—)

<Etherification> Synthesis of TDMIM

Toluene (36 g) was added to MIM (1.8 g, 8.1 mmol), potassium hydroxide (3.6 g, 64.8 mmol) and Decenyl-Ms (11.4 g, 48.6 mmol) were further added, and the mixture was stirred at 25° C. for 5 min. The mixture was heated to 80° C. and stirred for 14 hr. By TLC analysis (eluent: chloroform, phosphoric acid-copper sulfate color development), it was confirmed that the residual amount of Decenyl-Ms was less than 10%, and the reaction was discontinued. Toluene (42 mL) and ion exchange water (72 mL) were added to the reaction solution and the mixture was stirred at 20° C. for 10 min and stood for 10 min to allow for layer separation. The aqueous layer was removed, and the mixture was washed again with water. Then, 20 wt % brine (72 mL) was added, the mixture was stirred for 10 min and stood for 10 min to allow for layer separation, and the aqueous layer was removed. The obtained organic layer was subjected to a dehydrating treatment by adding anhydrous magnesium sulfate (3.6 g). Insoluble materials were filtered off using filter paper, and the solvent in the filtrate was evaporated by an evaporator to give a brown liquid (7.5 g).

The obtained brown liquid (7.5 g) was purified by silica gel column chromatography (eluent: hexane/ethyl acetate=100/0-98.5/1.5 (v/v)) to give TDMIM (5.3 g). The obtained TDMIM was analyzed for $^1$H-NMR (600 MHz, CDCl$_3$) and confirmed to be the object product.

$\delta$0.89 ppm (t, 12H, C$\underline{H}_3$—CH$_2$—), $\delta$1.26-1.38 ppm (m, 24H, CH$_3$—C$\underline{H}_2$—C$\underline{H}_2$—C$\underline{H}_2$—), $\delta$1.38 ppm (s, 6H, —O—C(C$\underline{H}_3$)$_2$—O—), $\delta$1.63 ppm (m, 8H, —C$\underline{H}_2$—CH$_2$—O—), $\delta$2.02 ppm (q, 8H, CH$_3$—CH$_2$—CH$_2$—C$\underline{H}_2$—CH$_2$—), $\delta$2.77 ppm (t, 8H, —C$\underline{H}_2$—CH$_2$—CH$_2$—O—), $\delta$3.54-3.41 ppm (m, 10H, —CH$_2$—C$\underline{H}_2$—O—, —O—CH$_2$—C$\underline{H}$—CH—O—C(CH$_3$)$_2$—), $\delta$3.67 ppm (m, 4H, —O—C H₂—CH—CH—O—C(CH₃)₂—), δ4.06 ppm (d, 2H, —O—CH₂—CH—CH—O—C(CH₃)₂—), δ5.40-5.31 ppm (m, 16H, —CH=CH—CH₂—CH=CH—)

<Deprotection> Synthesis of TDM

To TDMIM (5.0 g, 6.5 mmol) were added ethanol (50 mL), ion exchange water (4.6 g, 258.0 mmol) and hydrochloric acid (4 M dioxane solution) (16.1 mL, 64.5 mmol), and the mixture was stirred at 60° C. for 3 hr. By TLC analysis (eluent: chloroform/methanol=99.5/0.5 (v/v), phosphoric acid-copper sulfate color development), it was confirmed that TDMIM and an intermediate monoisopropylidene form disappeared, and the reaction was discontinued. To the reaction mixture was added hexane (50 mL), and the mixture was stirred at 25° C. for 10 min, and stood for 10 min to allow for layer separation. The upper layer (hexane layer) was recovered, and acetonitrile (50 mL) was added thereto. The mixture was stirred at 25° C. for 10 min, and stood for 10 min to allow for layer separation. The acetonitrile layer was removed and the mixture was washed again with acetonitrile. The solvent in the obtained hexane layer was evaporated to give a faint brown liquid (4.1 g).

The obtained faint brown liquid (4.0 g) was purified by silica gel column chromatography (eluent: hexane/ethyl acetate=98/2-95/5 (v/v)) to give TDM (2.6 g).

The obtained TDM was analyzed for ¹H-NMR (600 MHz, CDCl₃) and confirmed to be the object product.

δ0.89 ppm (t, 12H, CH₃—CH₂—), δ1.25-1.35 ppm (m, 24H, CH₃—(CH₂)₃—), δ1.63 ppm (m, 8H, —CH₂—CH₂—O—), 2.01 ppm (q, 8H, CH₃—(CH₂)₃—CH₂—), δ2.77 ppm (t, 8H, —CH₂—CH₂—CH₂—O—), 3.26-3.84 ppm (m, 18H, —O—CH₂—CH—CH—OH, —CH₂—CH₂—O—), 5.33-5.38 ppm (m, 8H, —CH=CH—)

<Esterification> Synthesis of TDM Diacrylate Form

TDM (500 mg, 0.68 mmol) and triethylamine (275 mg, 2.72 mmol) were added to dehydrating toluene (5.0 g) and the mixture was stirred. Thereto was added dropwise a solution of acryloyl chloride (246 mg, 2.72 mmol) in dehydrating toluene (1.0 g). The mixture was stirred at 25° C. for 1 hr, and the precipitate was collected by filtration to give a toluene solution of a TDM diacrylate form.

<Amination>

To a toluene solution of the TDM diacrylate form was added 2.0 M dimethylamine/tetrahydrofuran solution (1.7 ml, dimethylamine 3.40 mmol) and the mixture was stirred at 70° C. for 1 hr. The reaction solution was cooled to 25° C., 10 wt % brine (5.0 g) was added and the mixture was stirred for 10 min, stood for 10 min to allow for layer separation. The lower layer (aqueous layer) was removed. To the upper layer (toluene layer) was added 25 wt % brine (5.0 g) and the mixture was stirred for 10 min, and stood for 10 min to allow for layer separation. The lower layer (aqueous layer) was removed, and the upper layer (toluene layer) was dehydrated over anhydrous magnesium sulfate (500 mg) and filtered, and the filtrate was concentrated to give a faint yellow liquid (406 mg).

300 mg from the obtained faint yellow liquid was purified by silica gel chromatography (eluent: hexane/ethyl acetate=99/1-95/5 (v/v)) to give TDM-C3-DMA (241 mg).

The obtained TDM-C3-DMA was analyzed for ¹H-NMR (600 MHz, CDCl₃) and confirmed to be the object product.

δ0.89 ppm (t, 12H, CH₃—CH₂—), δ1.27-1.38 ppm (m, 24H, CH₃—(CH₂)₃—), δ1.63 ppm (m, 8H, —CH₂—CH₂—O—), 2.01 ppm (q, 8H, CH₃—(CH₂)₃—CH₂—), δ2.23 ppm (s, 12H, —N—(CH₃)₂), δ2.49 ppm (t, 4H, —O—CO—CH₂—CH₂—), δ2.60 ppm (m, 4H, —O—CO—CH₂—CH₂—), δ2.77 ppm (t, 8H, —CH₂—CH₂—CH₂—O—), δ3.43 (m, 8H, —CH₂—CH₂—O—), δ3.53 ppm (m, 6H, —O—CH₂—CH—CH—O—CO—), δ5.39-5.30 ppm (m, 10H, —CH=CH—, —O—CH₂—CH—CH—O—CO—)

[Example 5] (Synthesis of TLMES-C3-DMA)

<Esterification> Synthesis of DTBDPS-TLMES

DTBDPS-M (4.0 g, 6.1 mmol), linoleic acid (manufactured by NOF CORPORATION, purity≥99%) (9.4 g, 33.4 mmol) and DMAP (0.7 g, 6.1 mmol) were dissolved in chloroform (45 mL). Thereto was added EDC (7.6 g, 39.5 mmol), and the mixture was stirred at 30° C. for 5 hr. Disappearance of DTBDPS-M and an intermediate monotriester form was confirmed by TLC analysis (eluent: chloroform, superphosphoric acid-copper sulfate color development), and the reaction was terminated. The solvent in the reaction solution was evaporated, and dissolved in hexane (60 mL). To the hexane solution was added acetonitrile (30 mL), and the mixture was stirred at 25° C. for 10 min, and stood for 10 min to allow for layer separation. The hexane layer was recovered, and the solvent was evaporated to give a faint yellow liquid (11.1 g).

The obtained faint yellow liquid (10.0 g) was purified by silica gel chromatography (eluent: hexane/ethyl acetate=99.5/0.5-99/1 (v/v)) to give DTBDPS-TLMES (6.8 g).

The obtained DTBDPS-TLMES was analyzed for ¹H-NMR (600 MHz, CDCl₃) and confirmed to be the object product.

δ0.89 ppm (t, 12H, CH₃—CH₂—), δ1.03 ppm (s, 18H, (CH₃—)₃C—), δ1.25-1.37 ppm (m, 64H, CH₃—(CH₂)₃—, =CH—(CH₂)₄—CH₂—CH₂—), δ1.47-1.54 ppm (m, 8H, —CH₂—CH₂—CO—O—), δ2.04 ppm (q, 16H, —CH₂—CH₂—CH=CH—), δ2.11-2.32 (m, 8H, CH₂—CO—O—), δ2.77 ppm (t, 8H, =CH—CH₂—CH=), δ3.62-3.74 ppm (m, 4H, —O—CH₂—CH—), δ4.99 ppm (m, 2H, —O—CH₂—CH—CH—), δ5.32-5.39 ppm (m, 16H, —CH=CH—CH₂—CH=CH—), δ5.57 ppm (m, 2H, —O—CH₂—CH—CH—), δ7.33-7.63 ppm (m, 20H, tBu-Si(-Ph)₂—)

<Deprotection> Synthesis of TLMES

DTBDPS-TLMES (3.00 g, 1.8 mmol) was dissolved in tetrahydrofuran, and the mixture was cooled to 5° C. with stirring. Acetic acid (manufactured by Kanto Chemical Co., Inc.) (0.7 g, 12.3 mmol) and TBAF (1 M tetrahydrofuran solution) (manufactured by Tokyo Chemical Industry Co., Ltd.) (10.5 mL, 10.5 mmol) were successively added dropwise so that the temperature would not exceed 10° C. After dropwise addition, the mixture was stirred at 25° C. for 7 hr. Disappearance of DTBDPS-TLMES and an intermediate monosilyl form was confirmed by TLC analysis (eluent: chloroform, phosphoric acid-copper sulfate color development), and the reaction was terminated. The reaction solution was diluted with chloroform (30 mL), 5 wt % aqueous sodium hydrogen carbonate solution (30 mL) was added, and the mixture was stirred at 25° C. for 10 min. After stirring, the mixture was stood for 10 min to allow for layer separation, and the organic layer was recovered. The obtained organic layer was further washed with ion exchange water (30 mL), and the solvent was evaporated to give a faint yellow liquid (3.0 g).

The obtained faint yellow liquid (2.8 g) was purified by silica gel chromatography (eluent: hexane/ethyl acetate=97/3-80/20 (v/v)) to give TLMES (1.9 g).

The obtained TLMES was analyzed for ¹H-NMR (600 MHz, CDCl₃) and confirmed to be the object product.

δ0.89 ppm (t, 12H, C$\underline{H}_3$—CH$_2$—), δ1.25-1.37 ppm (m, 64H, CH$_3$—(C$\underline{H}_2$)$_3$—, =CH—(C$\underline{H}_2$)$_4$—CH$_2$—CH$_2$—), δ1.61 ppm (m, 8H, —C$\underline{H}_2$—CH$_2$—CO—O—), δ2.04 ppm (q, 16H, —CH$_2$—C$\underline{H}_2$—CH=CH—), δ2.26-2.37 (m, 8H, —C$\underline{H}_2$—CO—O—), δ2.77 ppm (t, 8H, =CH—C$\underline{H}_2$—CH=), δ2.90-5.23 ppm (m, 8H, —O—C$\underline{H}_2$—C$\underline{H}$—C$\underline{H}$—), δ5.32-5.39 ppm (m, 16H, —C$\underline{H}$=C$\underline{H}$—CH$_2$—C$\underline{H}$=C$\underline{H}$—)

<Esterification> Synthesis of TLMES Diacrylate Form

TLMES (1.7 g, 1.4 mmol) and trimethylamine (0.6 g, 5.5 mmol) were added to dehydrating toluene (17 g), and the mixture was stirred at 25° C. Thereto was added dropwise a solution of acryloyl chloride (0.5 g, 5.5 mmol) in dehydrating toluene (3.4 g). After stirring at 25° C. for 1 hr, the precipitate was collected by filtration to give a toluene solution of a TLMES diacrylate form.

<Amination> Synthesis of TLMES-C3-DMA

To the toluene solution of the TLMES diacrylate form was added 2.0 M dimethylamine/tetrahydrofuran solution (6.9 mL, 13.8 mmol), and the mixture was stirred at 70° C. for 1 hr. The reaction solution was cooled to 25° C., 10 wt % brine (17 g) was added, and the mixture was stirred for 10 min and stood for 10 min to allow for layer separation. The lower layer (aqueous layer) was removed, 25 wt % brine (17 g) was added to the upper layer (toluene layer), and the mixture was stirred for 10 min, and stood for 10 min to allow for layer separation. The lower layer (aqueous layer) was removed, and the upper layer (toluene layer) was dehydrated over anhydrous magnesium sulfate (1.0 g) and filtered. The filtrate was concentrated to give a faint yellow liquid (1.4 g).

The obtained faint yellow liquid (1.4 g) was purified by silica gel chromatography (eluent: hexane/ethyl acetate=99/1-97/3 (v/v)) to give TLMES-C3-DMA (0.5 g).

The obtained TLMES-C3-DMA was analyzed for $^1$H-NMR (600 MHz, CDCl$_3$) and confirmed to be the object product.

δ0.89 ppm (t, 12H, C$\underline{H}_3$—CH$_2$—), δ1.25-1.37 ppm (m, 64H, CH$_3$—(C$\underline{H}_2$)$_3$—, =CH—(C$\underline{H}_2$)$_4$—CH$_2$—CH$_2$—), δ1.61 ppm (m, 8H, —C$\underline{H}_2$—CH$_2$—CO—O—), δ2.06 ppm (q, 16H, —CH$_2$—C$\underline{H}_2$—CH=CH—), δ2.22-2.36 (m, 20H, —(CH$_2$)$_6$—C$\underline{H}_2$—CO—O—, (C$\underline{H}_3$)$_2$—N—), δ2.47-2.64 ppm (m, 8H, (C$\underline{H}_3$)$_2$—N—(C$\underline{H}_2$)$_2$—CO—O—), δ2.78 ppm (t, 8H, =CH—C$\underline{H}_2$—CH=), δ4.04 ppm, δ4.30 ppm, δ5.11 ppm, δ5.47 ppm (m, 8H, —O—C$\underline{H}_2$—C$\underline{H}$—C$\underline{H}$—), δ5.32-5.39 ppm (m, 16H, —C$\underline{H}$=C$\underline{H}$—CH$_2$—C$\underline{H}$=C$\underline{H}$—)

[Example 6] Preparation of Various MENDs (1) Formation of Nucleic Acid Electrostatic Complex Composed of siRNA and Protamine siRNA (Hokkaido System Science Co., Ltd.) was dissolved in Ultrapure DNase/RNase-Free distilled water (Invitrogen; Thermo Fischer Scientific) at 2 mg/mL, 4 mg/mL, and siRNA solutions were prepared.

As a vector core, the siRNA solution and a protamine solution (CALBIOCHEM; Merck Nihon Millipore K.K.) were diluted with 10 mM HEPES buffer to 0.3 mg/mL, 0.2 mg/mL, respectively, and 0.2 mg/mL protamine (250 µL) was added dropwise by a small portion while stirring 0.3 mg/mL siRNA (250 µL), whereby an electrostatic complex of siRNA and protamine (hereinafter to be referred to as "siRNA complex") was prepared (N/P ratio=1.0).

As the sequence of siRNA for Factor VII (hereinafter to be referred to as "FVII"), one described in Akinc et al., Molecular Therapy, 17(5), 872-879 (May 2009) (without chemical modification) was used.

(2) Preparation of siRNA Encapsulating MEND (as Cationic Lipid, TLM-C2-DMA, TLM-C3-DMA, TLM-04-DMA, TDM-C3-DMA, TLMES-03-DMA, DLinDAP, DODAP were Used Singly)

A 90% butanol solution of cationic lipid (TLM-C2-DMA (Example 1), TLM-C3-DMA (Example 2), TLM-C4-DMA (Example 3), TDM-C3-DMA (Example 4), TLMES-C3-DMA (Example 5), DLinDAP (Comparative Example 1), DODAP (Comparative Example 2)) and Chol solution were mixed in a 1.7 mL tube at a molar ratio of cationic lipid:Chol=7:3 to total lipid 3000 nmol. Furthermore, as PEG lipid, PEG2000-DMG solution was added at 3 mol % relative to the total lipid, and 90% butanol was added to the total amount of 400 µL to give a lipid solution. Separately, in a 1.7 mL tube, a siRNA complex (siRNA content: 160 µg) and 20 mM citrate buffer (pH 4) containing 130 mM NaCl are mixed to a total of 114 µL, whereby a siRNA solution was prepared. The siRNA solution was added to and mixed with the lipid solution while stirring by a vortex mixer. The total amount of the mixed solution was taken in a 1 mL syringe (27G), and slowly injected into citrate buffer (2 mL) under vigorous stirring (5 mL tube). The mixture was diluted with phosphate buffered saline (hereinafter to be referred to as "PBS"), subjected to ultrafiltration (1000 g, 15 min, 30° C.) using Amicon Ultra-15 100K device (Merck Nihon Millipore K.K.), and concentrated. Then, the mixture was diluted with PBS, applied to ultrafiltration again and concentrated. Lastly, the mixture was adjusted to a desired lipid concentration with PBS to give siRNA encapsulating MEND. MEND prepared by this operation is hereinafter referred to as "TLM-C2-DMA MEND", "TLM-C3-DMA MEND", "TLM-C4-DMA MEND", "TDM-C3-DMA MEND", "TLMES-C3-DMA MEND", "DLinDAP MEND" or "DODAP MEND", according to the cationic lipid used.

(3) Preparation of siRNA Encapsulating MEND (Mixture of 2 Kinds of TLM-C2-DMA, TLM-C3-DMA, TLM-C4-DMA was Used as Cationic Lipid)

A 90% butanol solution of a lipid mixture of TLM-C2-DMA (Example 1), TLM-C3-DMA (Example 2), TLM-C4-DMA (Example 3) at a molar ratio described in Table 4 (TLM-CX-DMA mix) was mixed in a 1.7 mL tube at a molar ratio of cationic lipid:Chol=7:3 to total lipid 3000 nmol. Furthermore, as PEG lipid, PEG2000-DMG was added at 3 mol % amount relative to the total lipid, and 90% butanol was added to the total amount of 400 µL to give a lipid solution. Separately, in a 1.7 mL tube, a siRNA complex (siRNA content: 160 µg) and 10 mM malic acid buffer (pH 7.4) were mixed to a total of 50 µL, whereby a siRNA solution was prepared. The siRNA solution was added to and mixed with the lipid solution while stirring by a vortex mixer. The total amount of the mixed solution was taken in a 1 mL syringe (27G), and slowly injected into malic acid buffer (2 mL) under vigorous stirring (5 mL tube). The mixture was diluted with PBS, subjected to ultrafiltration (1000 g, 10 min, 30° C.) using Amicon Ultra-15 100K device (Merck Nihon Millipore K.K.), and concentrated. Then, the mixture was diluted with PBS, applied to ultrafiltration again and concentrated. Lastly, the solution was adjusted to a desired lipid concentration with PBS to give siRNA encapsulating MEND. MEND prepared by this operation is hereinafter referred to as "MEND 1", "MEND 2", "MEND 3", "MEND 4" according to the ratio of the cationic lipid used as described in Table 4.

TABLE 4

| MEND name | Lipids mixing ratio |
| --- | --- |
| MEND 1 | TLM-C2-DMA:TLM-C3-DMA = 0.21:0.79 |
| MEND 2 | TLM-C3-DMA:TLM-C4-DMA = 0.75:0.25 |
| MEND 3 | TLM-C3-DMA:TLM-C4-DMA = 0.50:0.50 |
| MEND 4 | TLM-C3-DMA:TLM-C4-DMA = 0.25:0.75 |

(4) Preparation of mRNA Encapsulating MEND by Ethanol Dilution Method (TLM-C3-DMA, TDM-C3-DMA were Used Singly)

A 99.5% ethanol solution of cationic lipid (TLM-C3-DMA (Example 2), TDM-C3-DMA (Example 4)) was mixed in a 5 ml tube at a ratio of cationic lipid:DOPE:Chol=3:3:4 to total lipid 131 nmol. As PEG lipid, PEG2000-DMG was added at 3 mol % relative to total lipid to a total amount of 30 mL. Four tubes of these were prepared. In a 1.5 ml tube prepared separately was added 3 mg of mRNA encoding luciferase (prepared using mMessage mMachine T7 Ultra Transcription kit (Life Technologies Corporation)), 20 mM malic acid buffer (pH 3.0) containing 30 mM NaCl was added to a total amount of 45 ml. Four tubes of these were prepared similar to the lipid solution.

The lipid solution was mixed with the mRNA solution while vortexing, 925 ml of 100 mM 2-morpholinoethane-sulfonic acid (hereinafter to be referred to as "MES") buffer (pH 5.5) was successively added and mixed, and the mixture was decanted to Vivaspin turbo 15 (manufactured by Sartorius, hereinafter to be referred to as "Vivaspin") added with 2 ml of MES buffer in advance. The 5 ml tube was washed well with 2 ml of MES buffer by vortexing, and similarly decanted to Vivaspin. This operation was repeated 4 times, 2 ml of MES buffer was directly added to Vivaspin lastly, and the mixture was centrifuged and ultrafiltered at 25° C., 1000 g. Furthermore, PBS was added to sufficient dilute the mixture, and ultrafiltered under the same conditions. The solution was adjusted to a desired concentration with PBS to give mRNA encapsulating MEND. MEND prepared by this operation is hereinafter referred to as "TLM-C3-DMA mMEND", "TDM-C3-DMA mMEND", according to the cationic lipid used.

As the sequence of mRNA encoding luciferase, one described in "SUPPLEMENTARY DATA" of Miura et al., Nucleic Acids Research, 43(3), 1317-1331 (2015) was used.

[Example 7] Measurement of Particle Size, Dispersion Degree, Surface Electric Potential, siRNA Encapsulation Rate, siRNA Recovery Rate of Various MENDs The particle size, dispersion degree and surface electric potential of various MENDs were measured by a dynamic light scattering method (ZetasizerNano; Malvern instruments Ltd.).

The siRNA encapsulation rate and siRNA recovery rate were measured using RiboGreen (Invitrogen; Thermo Fisher Scientific). Various MENDs prepared in Example 6(2) or (3) were diluted with 10 mM HEPES buffer (pH 7.4) to 1000 ng/mL and used as sample solutions. In addition, siRNA complex used for the preparation of MEND was serially diluted to 0-2000 ng/mL with 10 mM HEPES buffer (pH 7.4) and used as analytical curve solutions. Separately from these solutions, dextran sulfuric acid, Triton X-100, Ribogreen were each diluted with 10 mM HEPES buffer to 0.08 mg/mL, 0.4%, 5 µL/mL, respectively, and measurement solutions were prepared. Also, one replacing Triton X-100 with 10 mM HEPES buffer was prepared. The analytical curve solution or sample solution (50 µL) was added to a 96 well plate, a measurement solution (50 µL) containing or not containing Triton X-100 was further added, and the mixture was stirred at 700 rpm for 5 min, after which fluorescence intensity was measured at excitation wavelength 500 nm and observed wavelength 525 nm. The siRNA amount measured under conditions containing Triton X-100 was divided by 1000 ng/mL to calculate siRNA recovery rate. The siRNA amount measured under conditions not containing Triton X-100 was subtracted from the siRNA amount measured under conditions containing Triton X-100, and the value was divided by siRNA amount measured under conditions containing Triton X-100 to calculate siRNA encapsulation rate.

The results are shown in Table 5 and Table 6.

TABLE 5

| MEND name | average particle size (nm) | dispersion degree | surface electric potential (mV) | siRNA recovery rate (%) | siRNA encapsulation rate (%) |
| --- | --- | --- | --- | --- | --- |
| TLM-C2-DMA MEND | 125 | 0.10 | −12 | 81 | 79 |
| TLM-C3-DMA MEND | 133 | 0.07 | −3 | 89 | 83 |
| TLM-C4-DMA MEND | 132 | 0.11 | 7 | 86 | 86 |
| TDM-C3-DMA MEND | 130 | 0.14 | −4 | 79 | 97 |
| TLMES-C3-DMA MEND | 145 | 0.07 | −5 | 79 | 91 |
| DLinDAP MEND | 98 | 0.23 | −3 | 82 | 67 |
| DODAP MEND | 98 | 0.22 | −4 | 90 | 70 |

TABLE 6

| MEND name | average particle size (nm) | dispersion degree | surface electric potential (mV) | siRNA recovery rate (%) | siRNA encapsulation rate (%) |
| --- | --- | --- | --- | --- | --- |
| MEND 1 | 122 | 0.08 | 0.24 | 79.4 | 91 |
| MEND 2 | 126 | 0.07 | 0.16 | 82.3 | 92 |
| MEND 3 | 122 | 0.08 | −0.12 | 84.4 | 94 |
| MEND 4 | 122 | 0.08 | −0.02 | 76.5 | 95 |

[Example 8] pKa Evaluation of MEND 20 mM citrate buffer, sodium phosphate buffer and tris HCl buffer containing NaCl at a final concentration of 150 mM adjusted to various pH values in the range of pH 3.0-10.0 were prepared. To these buffers were added MEND prepared in Example 6(2) or (3) to a lipid concentration of 30 µM, and 6-(p-toluidino)-2-naphthalenesulfonic acid sodium salt was added at 6 µM to make the final volume 100 µL. Thereafter, the fluorescence intensity was measured at an excitation wavelength 321 nm and an observed wavelength 447 nm at 37° C. The relative fluorescence intensity was calculated in percentage with the maximum value of fluorescence intensity in each MEND as 100% and the minimum value as 0%. The pH at which the relative fluorescence intensity was 50% was taken as pKa. The results are shown in Table 7 and Table 8.

TABLE 7

| MEND name | pKa of MEND |
|---|---|
| TLM-C2-DMA MEND | 4.67 |
| TLM-C3-DMA MEND | 5.89 |
| TLM-C4-DMA MEND | 6.83 |
| TDM-C3-DMA MEND | 6.14 |
| TLMES-C3-DMA MEND | 5.78 |
| DLinDAP MEND | 5.34 |
| DODAP MEND | 5.44 |

TABLE 8

| MEND name | pKa of MEND |
|---|---|
| MEND 1 | 5.81 |
| MEND 2 | 6.28 |
| MEND 3 | 6.56 |
| MEND 4 | 6.74 |

[Example 9] Membrane Fusion Ability Test of TLM-C2-DMA MEND, TLM-C3-DMA MEND, TLM-C4-DMA MEND, TDM-C3-DMA MEND, TLMES-C3-DMA MEND Blood was collected from male ICR mice, and red blood cells were collected and suspended in physiological saline. Physiological saline containing a given amount of red blood cells was added to PBS (pH 7.4) or 10 mM phosphate-10 mM malate buffered saline (pH 6.5, 5.5). Then, the PBS solution containing MEND prepared in Example 6(2) was added to a lipid final concentration of 300 μmol/L. Negative control (NC) was prepared by adding the same amount of PBS not containing MEND, and positive control (PC) was prepared by adding the same amount of PBS not containing MEND, and adding Triton X-100 to a final concentration of 0.02% (w/v) to dissolve red blood cells. These were incubated at 37° C. for 45 min, and centrifuged at 4° C., 400×g conditions for 5 min. The supernatant was recovered and the absorbance at 545 nm was measured to quantify the amount of hemoglobin leakage from the red blood cells. Subsequently, the measured value of each sample was expressed in percentage based on the measured value of PC as 100% (hemolysis activity). The higher the percentage, the higher the membrane fusion ability.

The results are shown in FIG. 1. TLM-C2-DMA MEND, TLM-C3-DMA MEND, TLM-C4-DMA MEND, TDM-C3-DMA MEND, TLMES-C3-DMA MEND showed higher membrane fusion ability as compared to DODAP MEND, DLinDAP MEND. Particularly, TLM-C3-DMA MEND, TLMES-C3-DMA MEND showed high membrane fusion ability at pH 5.5 alone.

[Example 10] Membrane Fusion Ability Test of MEND 1, MEND 2, MEND 3, MEND 4

Blood was collected from male ICR mice, and red blood cells were collected and suspended in physiological saline. PBS was adjusted to pH 7.4, 6.5, 5.5, and physiological saline containing a given amount of red blood cells was added. Then, TLM-C3-DMA MEND and TLM-C4-DMA MEND prepared in Example 6(2), and PBS containing MEND prepared in Example 6(3) were added at 3.3 μL, 10 μL and 30 μL, respectively. Negative control (NC) was prepared by adding the same amount of PBS not containing MEND, and positive control (PC) was prepared by adding the same amount of PBS not containing MEND, and adding Triton X-100 to 0.5% (w/v) to dissolve red blood cells. These were incubated at 37° C. for 30 min, and centrifuged at 4° C., 400×g conditions for 5 min. The supernatant was recovered and the absorbance at 545 nm was measured to measure the amount of hemoglobin. Subsequently, each measured value was expressed in percentage based on the measured value of PC as 100% (hemolysis activity). The higher the percentage, the higher the membrane fusion ability.

Figure 2:
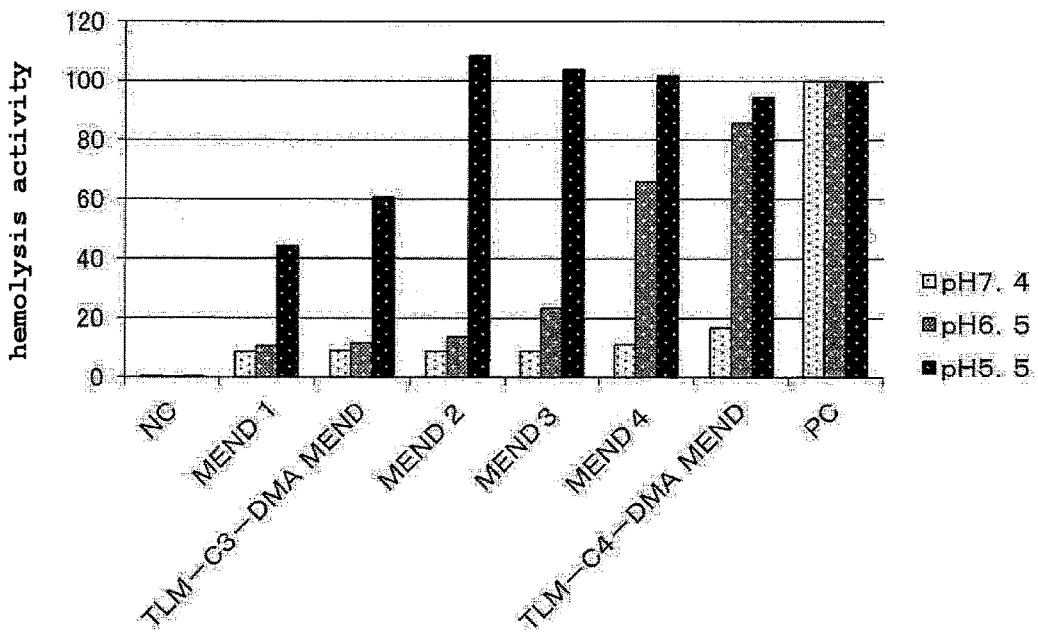
FIG. 2 is a graph showing the hemolysis activity of MEND 1-4, TLM-C3-DMA MEND, TLM-C4-DMA MEND.

The results are shown in FIG. 2. MEND 2, MEND 3, MEND 4 showed higher membrane fusion ability than TLM-C3-DMA MEND. Particularly, MEND 2 showed high membrane fusion ability at pH 5.5 alone as compared to MEND 3, MEND 4.

[Example 11] In Vivo Knockdown Activity Test of TLM-C2-DMA MEND, TLM-C3-DMA MEND, TLM-C4-DMA MEND, DLinDAP MEND, DODAP MEND A solution containing MEND prepared by the method shown in Example 6(2) was administered to 4-week-old male mice at 0.5 mg/kg from the tail vein. After 24 hr, the blood was collected, the blood sample was centrifuged at 1000 g for 10 min at 4° C., and the supernatant was recovered to give plasma. The amount of Factor VII(FVII) in the plasma was quantified using BIOPHEN FVII CHROMOGENIC ASSAY (Sysmex BioMed), and the FVII expression level of the MEND administration group was shown as a relative value (relative FVII amount in plasma) with the FVII expression level of the untreated group (NT) as 1.

Figure 3:
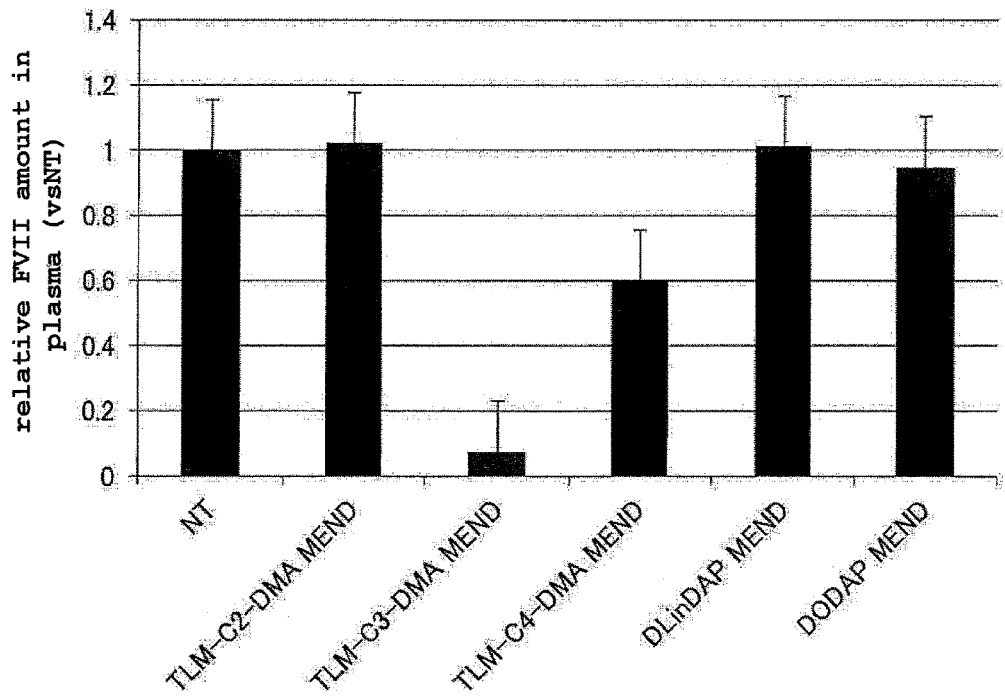
FIG. 3 is a graph showing the FVII knockdown activity by TLM-C2-DMA MEND, TLM-C3-DMA MEND, TLM-C4-DMA MEND, DLinDAP MEND, DODAP MEND.

The results are shown in FIG. 3. TLM-C3-DMA MEND, TLM-C4-DMA MEND showed decrease in the FVII expression level as compared to DLinDAP MEND, DODAP MEND. Particularly, TLM-C3-DMA MEND showed the highest knockdown activity.

[Example 12] In Vivo Knockdown Activity Test of TLM-C3-DMA MEND, TDM-C3-DMA MEND, TLMES-C3-DMA MEND A solution containing MEND prepared by the method shown in Example 6(2) was administered to 4-week-old male mice at 0.1 mg/kg from the tail vein. After 24 hr, the blood was collected, the blood sample was centrifuged at 1000 g for 10 min at 4° C., and the supernatant was recovered to give plasma. The amount of Factor VII(FVII) in the plasma was quantified using BIOPHEN FVII CHROMOGENIC ASSAY (HYPHEN BioMed), and the FVII expression level of the MEND administration group was shown as a relative value (relative FVII amount in plasma) with the FVII expression level of the untreated group (NT) as 1.

Figure 4:
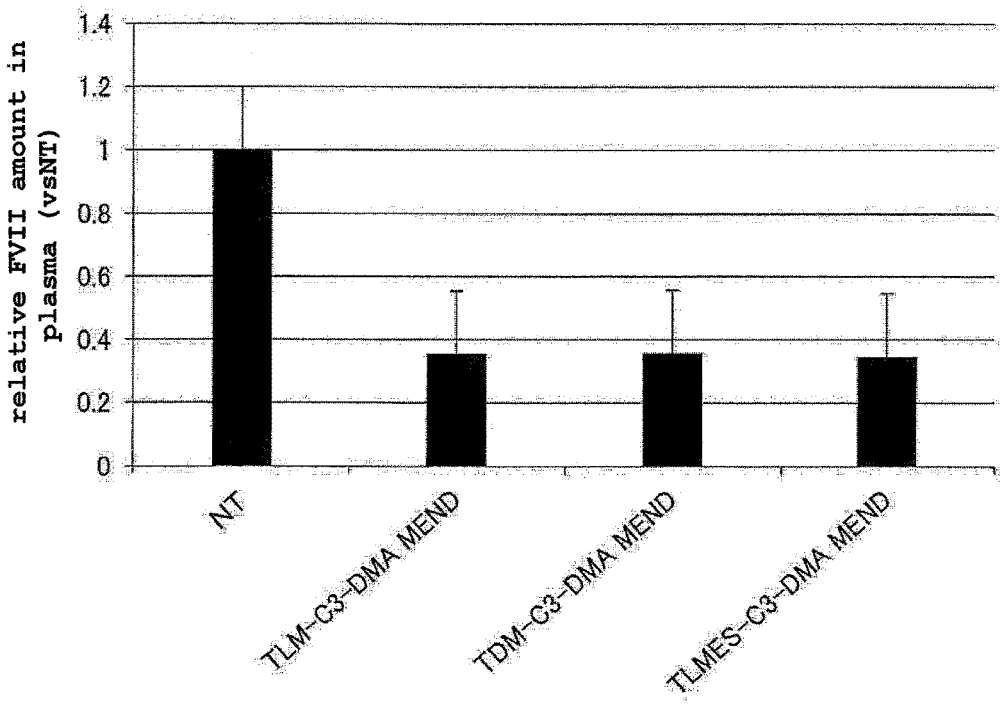
FIG. 4 is a graph showing the FVII knockdown activity by TLM-C3-DMA MEND, TDM-C3-DMA MEND, TLMES-C3-DMA MEND.

The results are shown in FIG. 4. TDM-C3-DMA MEND, TLMES-C3-DMA MEND also showed decrease in the FVII expression level, and showed almost equivalent knockdown activity as compared to TLM-C3-DMA MEND.

[Example 13] In Vivo Knockdown Activity Test of TLM-C3-DMA MEND, TLM-C4-DMA MEND, and MEND 1, MEND 2, MEND 3, MEND 4

TLM-C3-DMA MEND solution and TLM-C4-DMA MEND solution prepared by the method shown in Example 6(2) and MEND solution prepared by the method shown in Example 6(3) were administered to 4-week-old male mice at 0.1 mg/kg from the tail vein. After 24 hr, the blood was collected, the blood sample was centrifuged at 1000 g for 10 min at 4° C., and the supernatant was recovered to give plasma. The amount of Factor VII(FVII) in the plasma was quantified using BIOPHEN FVII CHROMOGENIC ASSAY (Sysmex BioMed), and the FVII expression level of the MEND administration group was shown as a relative value (relative FVII amount in plasma) with the FVII expression level of the untreated group (NT) as 1.

Figure 5:
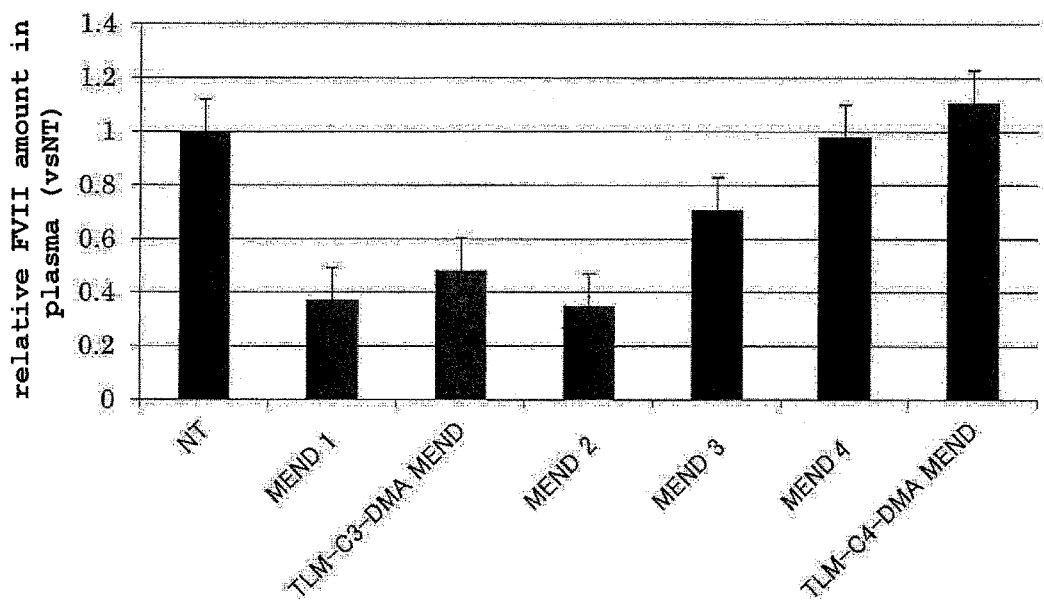
FIG. 5 is a graph showing the FVII knockdown activity by MEND 1-4, TLM-C3-DMA MEND, TLM-C4-DMA MEND.

The results are shown in FIG. 5. MEND 1, MEND 2 showed higher knockdown activity than TLM-C3-DMA MEND, and MEND 2 showed high and large knockdown activity.

[Example 14] mRNA Expression Test In Vivo

TLM-C3-DMA mMEND solution, TDM-C3-DMA mMEND solution prepared by the method shown in Example 6(4) were diluted with PBS such that mRNA was 1 mg/100 ml, and subcutaneously administered to the neck of 6-week-old female ICR mice. After 5.5 hr, a saline solution of luciferin (VivoGlo™ Luciferin, In Vivo Grade, manufactured by Promega) prepared in advance at 3 mg/200 ml/mouse was intraperitoneally administered to the mice, and 30 min later, the luminescence at the mRNA administration site was observed and quantified by IVIS™ LuminaII (Caliper Life Sciences).

Figure 6:
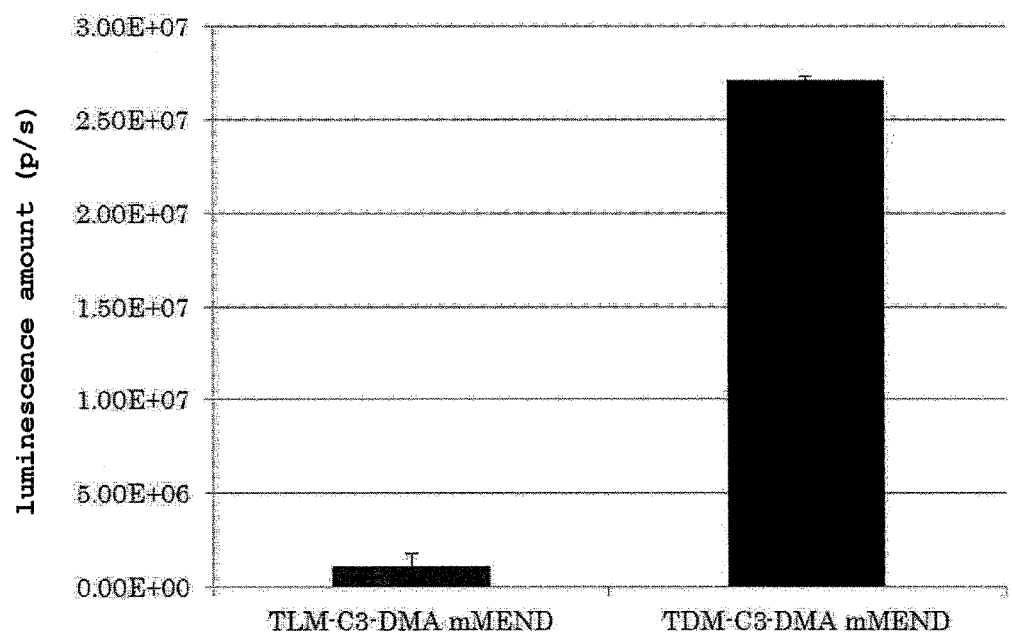
FIG. 6 is a graph showing the mRNA expression activity by TLM-C3-DMA mMEND, TDM-C3-DMA mMEND.

The results are shown in FIG. 6. Luminescence was confirmed in both TLM-C3-DMA mMEND and TDM-C3-DMA mMEND, and they showed mRNA expression activity. Of these, TDM-C3-DMA mMEND showed the strongest luminescence amount, thus showing high mRNA expression activity.

INDUSTRIAL APPLICABILITY

Since the agent of the present invention can delivery a functional nucleic acid into the cytoplasm with high efficiency, it is useful for developing nucleic acid pharmaceutical products and biochemical experiments.

This application is based on patent application No. 2014-166041 filed in Japan (filing date: Aug. 18, 2014), the contents of which are encompassed in full herein.

The invention claimed is:

1. A cationic lipid represented by the formula (1):

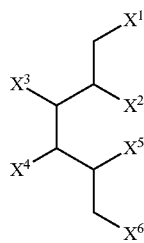
(1)

wherein any 4 of $X^1$-$X^6$ are each independently a group represented by the formula ($X^a$), a group represented by the formula ($X^b$) or a hydroxyl group (provided that said 4 are not hydroxyl groups at the same time), and the remaining 2 are each independently a group represented by the formula ($X^c$) or a hydroxyl group (provided that said 2 are not hydroxyl groups at the same time))

($X^a$)

wherein $R^1$ is an aliphatic hydrocarbon group having 8-22 carbon atoms or an acyl group having 8-22 carbon atoms; $Y^1$ is —O— or —NH—)

($X^b$)

wherein $R^2$ is a sterol residue or a liposoluble vitamin residue; $Z^1$ is an alkylene group having 2 or 3 carbon atoms; $Y^2$ is —O—CO— or —NH—CO—)

($X^c$)

wherein $R^3$ and $R^4$ are each independently an alkyl group having 1-6 carbon atoms, $R^3$ and $R^4$ are optionally bonded to form a ring; $Z^2$ is an alkylene group having 1-6 carbon atoms; $Y^3$ is —O—, —O—CO— or —NH—CO—; n is 0 or 1.

2. The cationic lipid according to claim 1, wherein any 4 of $X^1$-$X^6$ are each independently a group represented by the formula ($X^a$) or a group represented by the formula ($X^b$), and the remaining 2 are each independently a group represented by the formula ($X^c$).

3. The cationic lipid according to claim 1, wherein any 4 of $X^1$-$X^6$ are each independently a group represented by the formula ($X^a$), and the remaining 2 are each independently a group represented by the formula ($X^c$).

4. The cationic lipid according to claim 1, wherein $R^1$ is an aliphatic hydrocarbon group having 10-20 carbon atoms or an acyl group having 10-20 carbon atoms.

5. The cationic lipid according to claim 1, wherein $R^1$ is an aliphatic hydrocarbon group having an unsaturated bond and 10-20 carbon atoms or an acyl group having 10-20 carbon atoms.

6. The cationic lipid according to claim 1, wherein $Y^1$ is —O—.

7. The cationic lipid according to claim 1, wherein any 4 of $X^1$-$X^6$ are each independently a group represented by the formula ($X^b$), and the remaining 2 are each independently a group represented by the formula ($X^c$).

8. A lipid membrane structure comprising the cationic lipid according to claim 1.

9. A nucleic acid-introducing agent comprising the lipid membrane structure according to claim 8 and a nucleic acid.

* * * * *